(12) United States Patent
Fitzpatrick

(10) Patent No.: US 10,856,807 B2
(45) Date of Patent: Dec. 8, 2020

(54) SYSTEM AND METHOD FOR ANALYZING ITEMS USING IMAGE RECOGNITION, OPTICAL CHARACTER RECOGNITION, VOICE RECOGNITION, MANUAL ENTRY, AND BAR CODE SCANNING TECHNOLOGY

(71) Applicant: GODDESS APPROVED PRODUCTIONS LLC, New York, NY (US)

(72) Inventor: Catherine Fitzpatrick, New York, NY (US)

(73) Assignee: GODDESS APPROVED PRODUCTIONS, LLC, New York, NY (US)

( * ) Notice: Subject to any disclaimer, the term of this patent is extended or adjusted under 35 U.S.C. 154(b) by 0 days.

(21) Appl. No.: 16/021,191

(22) Filed: Jun. 28, 2018

(65) Prior Publication Data

US 2019/0000382 A1   Jan. 3, 2019

Related U.S. Application Data

(60) Provisional application No. 62/526,658, filed on Jun. 29, 2017.

(51) Int. Cl.
*G06K 9/20* (2006.01)
*A61B 5/00* (2006.01)
(Continued)

(52) U.S. Cl.
CPC ............ *A61B 5/681* (2013.01); *A61B 5/4866* (2013.01); *A61B 5/7267* (2013.01); *A61B 5/7475* (2013.01); *G06F 1/1613* (2013.01);

*G06F 19/00* (2013.01); *G06K 9/00671* (2013.01); *G06K 9/2081* (2013.01); *G06K 9/22* (2013.01);
(Continued)

(58) Field of Classification Search
CPC .... G06F 19/00; G06F 1/1613; G06K 2209/17
See application file for complete search history.

(56) References Cited

U.S. PATENT DOCUMENTS 8,606,652 B2 * 12/2013 Gonsalves ......... G06Q 30/0643
705/26.1
8,712,870 B2 * 4/2014 Baker ................ G06Q 30/0641
705/27.1
(Continued)

*Primary Examiner* — Seung H Lee
(74) *Attorney, Agent, or Firm* — Porzio Bromberg & Newman P.C.

(57) ABSTRACT

System and method for analyzing components of one or more items at a time based on the analysis of image data and item component data and deciphering that data for the user. A user can use a computing device for item data input and the system recognizes or identifies items by image recognition, optical character recognition, voice recognition, typed query, barcode scan or a combination of those to analyze the item and return analysis of each item to the user's computing device through visual display, audible communication or a combination of both visual display and audible communication. System and method for analyzing items, recognizing or identifying the images of items, and analyzing the components of items is executed by referencing image databases, image recognition services, application program interfaces (APIs) and through machine learning to provide the user with analysis of items by processing the data that corresponds with those items.

67 Claims, 16 Drawing Sheets

(51) Int. Cl.
  *G06F 19/00* (2018.01)
  *G06F 1/16* (2006.01)
  *G06K 9/00* (2006.01)
  *G06K 9/22* (2006.01)
  *A61B 5/11* (2006.01)
  *A61B 5/0205* (2006.01)

(52) U.S. Cl.
  CPC ........... *A61B 5/0205* (2013.01); *A61B 5/1118* (2013.01); *A61B 5/6898* (2013.01); *G06K 2209/17* (2013.01)

(56) References Cited

U.S. PATENT DOCUMENTS

| | | | |
|---|---|---|---|
| 9,254,099 B2 | 2/2016 | Connor | |
| 9,292,565 B2 * | 3/2016 | Bhagwan | G06K 9/18 |
| 9,875,258 B1 * | 1/2018 | Hsiao | G06F 16/532 |
| 2012/0300259 A1 * | 11/2012 | Hosaka | G11B 27/034 |
| | | | 358/1.15 |
| 2015/0379892 A1 * | 12/2015 | Sako | G06K 9/00597 |
| | | | 434/127 |
| 2016/0035248 A1 * | 2/2016 | Gibbs | G06T 7/0002 |
| | | | 434/127 |

* cited by examiner

SYSTEM AND METHOD FOR ANALYZING ITEMS USING IMAGE RECOGNITION, OPTICAL CHARACTER RECOGNITION, VOICE RECOGNITION, MANUAL ENTRY, AND BAR CODE SCANNING TECHNOLOGY

BACKGROUND OF THE INVENTION

According to the World Health Organization (WHO), cancer is one of the leading causes of morbidity and mortality worldwide, with approximately 14 million new cases in 2012; the number of new cases is expected to rise by about 70% over the next 2 decades; cancer is the second leading cause of death globally, and was responsible for 8.8 million deaths in 2015; and globally, nearly 1 in 6 deaths is due to cancer. According to the National Cancer Institute (NCI), approximately one-third of all U.S. Cancer cases are linked to food alone.

Cancer arises from the transformation of normal cells into tumor cells in a multistage process that generally progresses from a pre-cancerous lesion to a malignant tumor. These changes are the result of the interaction between a person's genetic factors and external agents, including chemical carcinogens, such as benzidine (a food additive). Also, according the to the Centers for Disease Control (CDC): chronic diseases and conditions such as heart disease, stroke; cancer, Type 2 diabetes, obesity, and arthritis are among the most common; costly, and preventable of all health problems. As of 2012, about half of all adults (117 million people) had one or more chronic health conditions; chronic diseases are responsible for 7 of 10 deaths each year, and treating people with chronic diseases accounts for 86% of our nation's health care costs; the total costs of heart disease and stroke in 2010 were estimated to be $315.4 billion. Of this amount, $193.4 billion was for direct medical costs, not including costs of nursing home care; cancer care cost $157 billion in 2010; and the total estimated cost of diagnosed diabetes in 2012 was $245 billion, including $176 billion in direct medical costs and $69 billion in decreased productivity.

Medical research has linked components in food and other items such as cosmetics, household cleaners, clothing, cooking equipment, sporting equipment, and the like to, for example, birth defects, developmental disorders, reproductive issues, migraines, allergies, skin conditions, blinding diseases, psoriasis, arthritis, endometriosis, Alzheimer's disease, obesity, multiple sclerosis, arterial disease, neuropathies, preeclampsia, erectile dysfunction, epilepsy, and narcolepsy.

With regard to food in terms of cancer, chronic diseases, illnesses and ailments, the problem is that it is extremely difficult to look at a food and tell if it is going to provoke a disease or prevent one. Ingredients on labels are extremely difficult to decipher. For instance, a doctor may tell a cancer or diabetes patient that they need to avoid added sugars, but the patient doesn't know all the different ways added sugar is listed on labels. According to the U.S. Department of Health and Human Services, added sugars show up on food and drink labels under the following names: anhydrous dextrose, brown sugar, cane crystals, cane sugar, corn sweetener, corn syrup, corn syrup solids, crystal dextrose, evaporated cane juice, fructose sweetener, fruit juice concentrates, high-fructose corn syrup, honey, liquid fructose, and malt syrup.

Foods, cosmetics, household products, clothing, and other items are known to contain substances and materials that the World Health Organization through its cancer research agency, International Agency for Research on Cancer (IARC), has classified as cancer-causing agents. Most consumers are not aware of the cancer-causing agents (also known as carcinogens) that the IARC has identified, for example, butylated hydroxyanisole, in order to identify these substances when they appear on labels. Also, this list of cancer-causing agents is constantly being updated as more research is found. Even if a consumer memorized the IARC's list and kept up with every update, there are numerous other terms that these cancer-causing agents appear as on labels. For instance, benzidine has been classified as a carcinogen by the IARC but the word "benzidine" rarely appears on food labels. Instead, "Red 40" and "Yellow 6," which contain benzidine appear on food labels. Many consumers are not aware of which ingredients contain carcinogens and, as a result, they are consuming carcinogens on a regular basis.

Foods that do not have nutrition labels, such as foods in the produce aisle, can contain components that could help consumers prevent cancer and other chronic diseases for example, antioxidants. The average consumer knows that vegetables are good for them, but they don't know which ones have more antioxidants than others, which could help them fight or avoid cancer. Many consumers do not know how much starch each type of vegetable contains, which could affect their insulin. Another example of items that consumers come across that do not have labels are items in the deli section of a grocery store, where multiple meat products contain nitrite, which is classified as a cancer-causing agent by the IARC.

U.S. Pat. No. 9,254,099 describes a device and system for monitoring a person's food consumption comprising a wearable sensor that automatically collects data to detect probable eating events; an imaging member that is used by the person to take pictures of food wherein the person is prompted to take pictures of food when an eating event is detected by the wearable sensor; and a data analysis component that analyzes these food pictures to estimate the types and amounts of foods, ingredients, nutrients, and calories that are consumed by the person. The wearable sensor can be part of a smart watch or smart bracelet. The imaging member can be part of a smart phone. The integrated operation of the wearable sensor and the imaging member disclosed in this invention offers measurement of food consumption with low intrusion into the person's privacy and can automatically log food items that have been identified as consumed by the user to a diet log. U.S. Pat. No. 9,254,099 has the shortcoming that it does not automatically log a user's physical activity based on the user's motions and movement to a physical activity or exercise log to allow users to keep track of their physical activity, caloric expenditure and the like.

MyFitnessPal is an app, which can run on a smartphone, for tracking calories and diet. MyFitnessPal allows users to add foods the user has consumed to a diet log through manual entry. MyFitnessPal can automatically record the number of steps a user has taken based on the motion of the user's phone and estimate the user's caloric consumption and expenditure. MyFitnessPal has the shortcoming that it is cumbersome for the user to manually enter data directed to foods and does not provide for the user to use the image sensor of a computing device to input and log foods the user has consumed or use the image sensor of a computing device to input and log exercise or physical activity.

Conventional methods do not allow users to customize the method used to analyze items according to the preferences and purchase patterns of another user or a prominent figure in society, such as a celebrity or athlete.

With regard to items beyond food, very few people know what substances have been used to manufacture the items they use every day. For example, many people do not know if their yoga mat, their children's toys, their pots and pans, their pet's food or the artificial turf on a ball field their child plays on contains substances or agents that could provoke or exacerbate cancer, a disease, allergy or ailment. It is also difficult to research thousands of products and each item's materials or ingredients to find and purchase alternative products that would be better for one's health.

There is a need to truly combat the world's diseases and ailments, for people to have a seamless and easy way to identify which items contain components that could either prevent or provoke a disease or condition, for people to have the ability to keep a record of the items they are using and consuming and to keep track of their physical activity. To make these tasks seamless and easy, it is desirable for each step to be coordinated on one interface. For instance, it is desirable for a person to be able to go to the store or open a cabinet at home and instantly see which items are best for their health and wellness goals, purchase those items easily at the store or from their computing device, have instant access to alternative items that are more favorable to their health, be able to purchase those alternative items easily as well as keep track of their product choices so they can purchase the items again. If the items purchased are food, it is desirable for people to be able to add those foods simultaneously to their diet log for assessment in comparison to their physical activity, receive information about how to cook the items and receive an easy to understand interpretation of what the serving sizes of those items look like and are, all on the same interface. There is a need for a centralized, quick and accurate way to calculate the calories, fat, sodium, etc. they are consuming and compare that to their physical activity in order to avoid or reverse weight gain, diseases and cancer. It is also desirable to provide a central interface where persons can keep track of not only their personal data, but also the data of others such as their children or spouse.

There is also a need in the medical research community to collect and track data for studies on the substances and ingredients people consume and are exposed to everyday and the links of those substances and ingredients to cancers, diseases and conditions, to advance medical research and discovery.

Retailers and manufacturers are also in need of shopping behavior information or data to know how to increase profits and adjust their market strategy.

Retailers, manufacturers, and government agencies are also in need of a system that can quickly target the locations of products that have been recalled in order to remove them from shelves to protect consumers. Retailers, manufacturers, and government agencies are also in need of a system that can trace incidents of illness and outbreaks, such as *e-coli* in order to track down the source of the outbreak and pinpoint which products need to be recalled.

Also, many consumers find it difficult to translate the serving sizes listed on labels into what that amount equates to on their plate. For example, many people will eat a bowl of cereal, assume that is the serving size, and think the amount of calories, sugar, sodium, etc. that they have consumed is the amount listed on the cereal box. However, the nutrition information that appears on the cereal box was calculated based on a serving size being ¾ of a cup of cereal, while the average cereal bowl holds three times that amount. As a result, many people are consuming triple the amount of calories, sugar, sodium, etc. than they think they are, which over time, can lead to weight gain, cancer, and chronic disease. It is desirable to provide a system that accurately calculates serving sizes.

Also, people who are blind, visually impaired, or illiterate cannot read labels on food and other items to interpret how these items will affect their health and what the serving size is. They need this information or data returned to them audibly.

Also, there are environmental items that we encounter in our everyday lives that can affect our health and risk of disease. For example, artificial turf is often installed in playgrounds, soccer fields, football fields, etc. It has been found that some types of these materials contain known carcinogens.

Also, over time, consumers have adopted a number of different lifestyles and philosophies and would like a convenient way to find and choose the items that are in line with their lifestyle choices and philosophies. For example, consumers who have adopted a vegan lifestyle, but have a difficult time identifying all the ingredients in a product to know if all the ingredients are vegan. In another example, consumers who are dedicated to supporting fair trade and protecting small-scale farmers, but have a difficult time identifying which items are fair trade and which ones are not. In another example, consumers who have learned that the palm oil industry is linked to deforestation, habitat degradation, climate change, animal cruelty and indigenous rights abuses in the countries where it is produced and want to avoid items containing palm oil but do not have the time to scour rows of ingredients on thousands of items to see which ones contain palm oil. Consumers are in need of a system that will evaluate items quickly, according to their needs and preferences.

Also, government entities are searching for solutions to enforce new regulations regarding labels. For example, the Federal Drug Administration is looking for ways to reduce the regulatory burden related to signage regarding calorie content in self-serve food, including buffets and grab-and-go foods, as well as ways to provide calorie information on something other than a restaurant menu to enforce "Food Labeling; Nutrition Labeling of Standard Menu Items in Restaurants and Similar Retail Food Establishments."

Also, consumers do not have the time or the access to research the conditions of farms, growers and processing plants to determine and compare how food is being grown, raised and processed from one farm to the next. Most consumers have to depend on various certifications such as "organic" issued by government entities and organizations to gauge how favorable a food is for their health. But these certifications are vague and do not offer consumers the information they need to make an informed choice. For instance, if pesticides have been applied to a plant or if a meat product came from an inhumanely treated animal. It is desirable to provide a system to include product origination.

SUMMARY OF THE INVENTION

The system for analyzing items of the present invention gives users quick access to information or data about items in front of them, by recognizing the item and analyzing the data that is pertinent to that item and the user's needs on an interface that is easy to understand.

The system allows users to hold a computing device that has an image sensor near one or more items or hold one or more items near a computing device that has an image sensor to identify and analyze the composition of the items. This method and system detects and identifies the items through image recognition, voice recognition, manual entry, and bar code scanning technology.

The system for analyzing items includes, but is not limited to, analyzing all foods whether they are in a store, on a plate, on a menu, in a picture, and the like. The system for analyzing items also analyzes items other than food such as cosmetics, toiletries, hair care supplies, household products (e.g. cleaning agents, detergents, air fresheners, etc.), clothing, bedding, toys, sporting goods (e.g. yoga mats), baby products (e.g. pacifiers, diapers, bottles, etc.) building materials (e.g. artificial turf, paint, wood), fertilizers, cooking equipment, buildings, structures, furniture, etc. The computing devices used to deploy this system of analyzing items include, but are not limited to, handheld devices such as smartphones, cellular phones, tablets, as well as computers, laptops, smart watches, smart glasses and other smart accessories. Using the image sensor of the computing device, the system for analyzing items recognizes and interprets items by either correlating them to the images of those items stored in databases, recalled through application program interfaces (API) or through pattern recognition and machine learning. Once this method and system detects, recognizes and analyzes an item, the system for analyzing items returns that analysis to the user on the computing device either through a visual display, audible communication, or both.

Item information or data that the system for analyzing items include, but are not limited to, an item's ingredients, materials, nutritional information, nutrients, antioxidants, substances, materials, location, price, recall status, etc. The system for analyzing items can analyze items by processing each item's data through one or more methods based on the user's needs, preferences, condition, etc. The system for analyzing items can return that analysis back to the user on a computing device visually, audibly or both visually and audibly. For example, the user receives a rating or score of each item to learn which items are the most favorable and the least favorable based on the user's needs, preferences, condition, etc.

The system for analyzing items allows users to compare items and see which ones have substances, ingredients and components that research has shown can either prevent or provoke cancer chronic disease, allergies, ailments and other conditions, along with which items are the most favorable and the least favorable based on the user's other needs, preferences, or both which may or may not pertain to their health such as the preference to purchase fair trade items.

The system for analyzing items can also allow users to customize the method used to analyze items by their preferences of lifestyle or philosophy. Examples of such preferences include, but are not limited to, vegan, organic, fair trade, Paleo, gluten-free, lactose-free, grass-fed, peanut-free, hormone-free, antibiotic-free, etc.

The system for analyzing items allows users to customize the method used to analyze items according to the user's specific needs. For example, a user with high blood pressure who wants sodium content in foods to be prioritized in the analysis and rated on a more vigilant scale; a user who wants to know if an item can be delivered and if so, from which businesses, at what prices, and in how much time they can expect the delivery to arrive; a user who wants to evaluate whether an item is in a recipe, on their shopping list, is favorable to their exercise plan or fitness goals or has been recalled, is under investigation or is included in a lawsuit.

These system for analyzing items allows users to input specific ingredients they either want in an item or do not want in an item. For instance, if a user does not want any items with rayon, soybean oil, palm oil, or peanuts, they can input those ingredients and materials into their computing device, which informs the user when any of those substances and ingredients are present in an item. Another example, a user who is looking for items that contain acai berry or wants items that are 100% cotton, the system for analyzing items can inform the user when those substances and ingredients are present in items.

The system for analyzing items allows the user to perform the transaction to purchase items that are recognized or identified by the system.

The system for analyzing items allows users to customize the method used to analyze items according to the preferences and purchase patterns of another user or a prominent figure in society such as a celebrity or athlete.

The system for analyzing items allows users to transfer item analysis to perform other tasks on a computing device including, but not limited to, purchasing items, purchasing alternative items, logging diet and physical activity, keeping track of purchases and spending, creating shopping lists, recipes, meal plans and exercise plans, accessing other users' recipes, communicating with other users about items, submitting and accessing cooking instructions and advice, submitting and accessing customer reviews of items, obtaining information about investigations, lawsuits, and recalls pertaining to items, and obtaining information about each item's serving size, location, cost, availability, location of origin, number purchased, manufacturing information, item comparison, frequency of item searched, frequency of an item purchased, price per unit, and the like.

The system for analyzing items provides consumers with a central interface—one tool—that will allow them to not only keep track of and analyze all of the items they use, eat, buy, and consume, but also seamlessly transfer those items into a food or diet log and a physical activity log to accurately assess their own and their family member's energy input and output. For example, a user can select an item that has been identified on their computing device and add it directly to their food or diet log. In another example, a user can use their computing device to recognize the yoga mat that they are about to use in yoga class, select the image of the yoga mat and add yoga as a physical activity to their fitness log to calculate caloric expenditure.

The system for analyzing items allows users to log their food intake, process the ingredients and nutritional data of those foods, and keep track of their energy expenditure. The system for analyzing items allows a user to track the personal data of multiple users including, but not limited to, their food intake and physical activity data by allowing users to sync their profiles with other users, manually input other users' data into the system for analyzing items or both automatically sync user profiles and manually enter user profile data. For example, a user who wants to keep track of one or more family members' food consumption and physical activity, along with their own, to help themselves and their family members meet their fitness and health goals. The system for analyzing items offers users an automated method to add foods to a diet log (i.e. once an item has been identified and analyzed by the system for analyzing items, the item can be automatically logged into a diet log). The system for analyzing items also automatically track a user's movement and can automatically log that movement and the equivalent caloric expenditure of that movement to the user's physical activity log.

The system for analyzing items allows users to set fitness goals and receive prompts in order to help them achieve those fitness goals. Examples include, but are not limited to, monitoring how many steps the user has taken, alerting the user to perform some sort of physical activity if the user has been stationary for a certain period of time, or alerting a user who is fasting when it is time to eat again. For example, a user is finished taking a yoga class and aims the image sensor of his computing device toward his yoga mat. The system for analyzing items identifies the yoga mat and allows the user to add "yoga" to his or her physical activity log as well as the caloric expenditure, cardiovascular benefits, musculoskeletal benefits, etc. of a yoga class to his or her physical activity log and personal record.

These system for analyzing items also presents users with information or data about "alternative items." "Alternative items" are defined as items that are not in the user's immediate presence but are available for use and purchase such as from an online retailer, another store, a farmer's market or another shelf in the same store as the user. The information or data about "alternative items" that the system for analyzing items presents to the user includes, but is not limited to, where the item can be purchased, the cost of the item, how to purchase the item, etc. The system for analyzing items allows the user to perform the transaction to purchase "alternative items" on the same interface using a computing device.

The system for analyzing items collects and analyzes data concerning purchases and consumption of items between a specific person and a reference population.

The system for analyzing items collects and analyzes item data and user data for private and public entities such as retailers, manufacturers, government agencies, medical facilities, etc. for large-scale data analysis. For example, this system and method will collect, store and analyze user data and item data including, but not limited to, consumer demographics, purchases, medical history, health status, biomedical information or data (heart rate, blood pressure, family history, etc.), prices, location, inventory, availability, product reviews, recipes, etc. Large-scale data analysis allows retailers and manufacturers to hone their business and marketing strategies and locate products, track inventory, analyze customer traffic, gauge customer interest, etc.

The system for analyzing items collects and analyzes item data and user data from for medical research to further scientific research and discovery. For example, a medical research facility is doing a comprehensive study on how a vegan diet affects a person's weight. This system for analyzing items can collect and analyze the data of all the users in the system who identify as vegan, kept a food log of the items they ate, and a log of their weight changes, and submit that data to the medical research facility that wants large-scale analysis.

Another example of how the system for analyzing items can collect and analyze item data and user data from users who have input their personal data into the system for analyzing items and have permitted the use of their data for medical research is a feature of the system for analyzing items that allows users to log symptoms and flare-ups of their conditions such as migraines, allergic reactions, rashes, lupus, psoriasis, hives, etc. These are just several examples of the thousands of aspects of a user's lifestyle, habits, conditions, and preferences that the system for analyzing items can collect and store as data. This health condition logging feature allows both the user and medical researchers to cross reference theses flare-ups to other aspects of the user's data such as shopping history, food or diet log, physical activity, etc. in order to try to trace a cause or possible cause of the user's symptoms and or flare-ups. For example, a medical researcher can query (further described in FIG. 14 description) "migraine log"+"food and activity log" in order to see—using the data of millions of users—if any correlations can be made between certain foods and activities that may contribute to or prevent migraine headaches.

The health condition logging feature of the system for analyzing items has numerous uses including, but not limited to, logging not only what foods the user eats, also what time the user eats the item, what type of physical activity the user performed, what time the physical activity was performed, where the physical activity was performed, and the like. This health condition logging feature allows for data across numerous subject matters to be aggregated and analyzed to discover correlations and possible causes of numerous conditions, diseases, ailments, allergies, etc.

For example, a medical researcher wants to investigate whether there is a link between cancer and users' exposure to artificial turf made from tire crumbs. In this example, data can be accessed from users who have input the duration and frequency of their own or their children's activity on various surfaces (artificial turf, grass, etc.) and have logged their own or their children's conditions, diseases, and ailments. By collecting user data on a macro scale offers medical researchers an abundance of data to cross-reference and identify correlations. In this example, researchers could see if there was any correlation between cancer cases and user exposure to artificial turf or the opposite: If cancer cases appeared just as frequently among users exposed to artificial turf as those who predominantly performed physical activity on natural grass or other surfaces.

The system for analyzing items can collect data such as quantities of items and the location of items for private and public organizations, as well as government entities when items are recalled. The system for analyzing items can track down items that have been recalled by their makers or manufacturers, signal users to the recalled items and provide an explanation to users as to why the items have been recalled. The system for analyzing items can perform this task in a number of ways including, but not limited to, employing a locator feature so that when a user launches the system for analyzing items using a computing device and analyzes an item that has been recalled, the location of that user and item is reported back to the system, allowing manufacturers and retailers to quickly pinpoint the locations of recalled items that are still on store shelves so they can quickly remove the recalled items to protect consumers' safety. An example of the kind of information or data businesses can benefit from the system for analyzing items is knowing the amount of times their product is considered by a customer and then, is either purchased by the customer or is passed over by the customer and knowing what that customer's other product choice was. Retailers and manufacturers can use this data for example, to figure out if they need to encourage customers to increase their purchase frequency of a product or if the marketing strategy should focus more on increasing the number of households that purchase the product.

The system for analyzing items can collect data about purchases of items and consumption of items so that in the event of an outbreak, such as an *e-coli* outbreak, the source of the outbreak, such as a certain farm, can be tracked down quickly and at-risk items can be removed for public safety.

The system for analyzing items can collect, store, analyze, and display information or data about items to assist public and private entities including, but not limited to, retailers, manufacturers, eating establishments and government entities to help them comply with and enforce federal, state, and local regulations. For example, the system for analyzing items 100 may be used by the United States Federal Drug Administration (FDA) to enforce the Nutrition Labeling of Standard Menu. Items in Restaurants and Similar Retail Food Establishments regulation. In another example, the system for analyzing items may assist the United States Department of Agriculture (USDA) identify which items meet the USDA's standards for classifications and certifications that include, but are not limited to, "Certified Organic," "Non-GMO," "Certified Vegan," "Fair Trade," "Kosher," etc.

The system for analyzing items can give users an option to receive item analysis audibly, which will allow people who are blind, visually impaired, or illiterate and cannot see or read labels on food and other items to be able to hear the analysis of an item so they can gauge how items will affect them.

The system for analyzing items can also analyze items that are submitted by users by scanning an item's bar code using the image sensor on a computing device. For example, a user can scan the bar code of an item and the system for analyzing items can analyze the item and return the analysis of that item to the user either visually or audibly through a computing device as well as visually and audibly at the same time. This additional feature of the system for analyzing items can give users another avenue to identify and analyze items that the system for analyzing items cannot detect or recognize through image recognition.

The system for analyzing items can also analyze items that are submitted by users manually. For example, a user can type in the name of an item and the system for analyzing items can analyze the item and return the analysis of that item to the user either visually or audibly through a computing device. This additional feature of system for analyzing items can allow users to identify and analyze items that the system for analyzing items cannot detect or recognize through a computing device's image sensor.

The system for analyzing items can also locate farms and retailers for users based on user location and user preferences. For example, a user who wants to know where the nearest organic farm is or where a store is that sells a product the user wants.

BRIEF DESCRIPTION OF THE DRAWINGS

This disclosure is illustrated by way of example and not by way of limitation in the accompanying figures. The figures may, alone or in combination, illustrate one or more embodiments of the disclosure. Elements illustrated in FIGS. 1 through 15 are not necessarily drawn to scale. Reference labels may be repeated among the figures to indicate corresponding or analogous elements.

FIG. 10 is a schematic diagram showing use of the system to transfer item information or data and analysis into other features of the system including, but not limited to, a food or diet and physical activity log, shopping list generator, recipe generator, medical record keeper, and the like.

DETAILED DESCRIPTION OF THE INVENTION

FIGS. 1 through 11 illustrate various examples of the use of the system for analyzing items 100 to analyze items based on item components. Components of items, which can be processed by system for analyzing items 100, include, but are not limited to, an item's nutritional information, ingredients, materials, method of being processed, source, environmental impact, price, rating, availability, location, and the like in order for the user to gauge where that item stands in terms of how favorable that item is to the user's lifestyle, health and fitness goals, standards, budgetary goals and the like.

Figure 1:
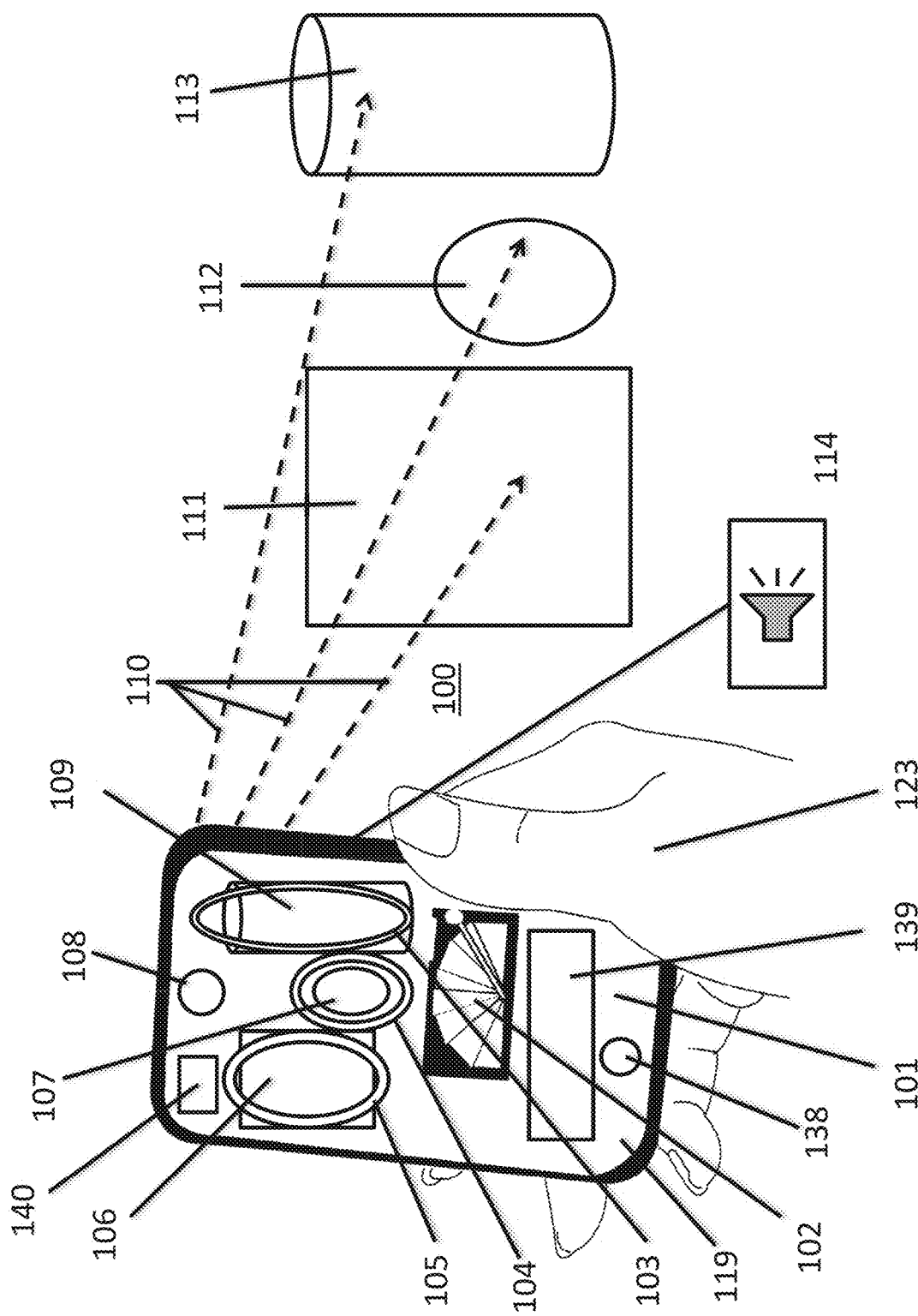
FIG. 1 is a schematic diagram of a system for analyzing items using a computing device with an image sensor to detect, recognize, and analyze items in which the items are physically present using image recognition.

FIG. 1 illustrates the use of the system for analyzing items 100 to recognize and analyze items 111, 112, 113 that are physically present and return that analysis to the user 123 through computing device 101 using image sensor 108 to detect the items 111, 112, 113. For example, image sensor 108 can be an optical lens. Computing device 101 includes, but is not limited to, smartphones, tablets, computers, laptops, smartwatches, smart glasses, virtual reality viewing devices and the like. In one embodiment, user 123 can hover computing device 101 near one or more items 111, 112, 113 or hover one or more items 111, 112, 113 near computing device 101 in order for image sensor 108 to recognize items 111, 112, 113 and return an analysis 103, 104, 105 of each item back to user 123.

FIG. 1 illustrates an example where items 111, 112 and 113 are being analyzed by system for analyzing items 100. For example, item 111 can be a box of cheese crackers. Item 112 can be an egg and item 113 can be a household cleaner spray. The dashed lines 110 illustrate the field of vision of image sensor 108 of computing device 101. In this example, computing device 101 has detected item 111, item 112, and item 113, which is evident by image 106 of item 111, image 107 of item 112 and image 109 of item 113 appearing on computing device 101. It will be appreciated that the system for analyzing items 100 can detect and distinguish between all variations of items, for example each brand, flavor, label, version, and the like. For example, system for analyzing items 100 can analyze the differences between all different kinds of crackers made by Brand X, Brand Y and Brand Z.

FIG. 1 illustrates an example of how user 123 receives analysis 103, 104, 105 of items 111, 112, 113. Analysis 103, 104, 105 can be communicated to user 123 in a number of ways including, but not limited to, numbers, colors, words and the like and can be displayed by computing device 101 on display 119 as a visual display, communicated by audible communication device 114, such as a speaker or both. In the example in FIG. 1, analysis 103, 104, 105 returned to user 123 is a "rating" of each item using a color-coded system to visually display each item's "rating" to user 123. In this example, analysis 103, 104, 105 are each displayed as ratings with rings of different colors encircling images of the corresponding items displayed on computing device 101. In this example, analysis 103, 104 and 105 are rings representing the rating of each item has received after system for analyzing items 100 processed the components of each item. In this example, analysis 103, 104, 105 illustrates different ratings each item has received which are displayed with different colored rings around each item's image on computing device 101. In this example, analysis 105 directed to item 111 is determined by the system to have a first color rating demonstrated by a first color ring encircling image 106 of item 111 on computing device 101. For example, the first color can be orange. In this example, analysis 104 directed to item 112 is determined by computing system 101 to have a second color rating demonstrated by a second color ring encircling image 107 of item 112 on computing device 101. For example, analysis 104 directed to item 112 is determined by computing system 101 to have an egg and a second color can be green. In this example, analysis 103 directed to item 113 is determined by the system to have a third color rating which is displayed on the computing device 101 as a third color ring encircling the image 109 of item 113 on computing device 101. For example, item 113 can be a household cleaner and the third color rating can be red.

System for analyzing items 100 can include a color-coded scale 102 displayed on the computing device 101 to show a comparison of colors provided by analysis 103, 104, 105 to understand what each color represents in terms of each item's rating. In this example, an item receives a fourth color rating, when system for analyzing items 100 has determined that the item is a favorable item for user 123. In this example, an item receives a third color rating, when system for analyzing items 100 has determined that the item is a mostly favorable item for user 123. In this example, an item receives a second color rating, when system for analyzing items 100 has determined that the item is a mostly unfavorable item for user 123. In this example, an item receives a first color rating, when this method and system have determined that the item is very unfavorable for user 123. In this example, the various shades or hues or intensities of these colors indicate where items fall along this color-coded scale of favorable to very unfavorable by shades or hues or intensities of the corresponding colors. For example, if the color-coded scale ranges from red indicating the most unfavorable items to green as the most favorable items, a dark orange rating would indicate that an item is less favorable for user 123 than an item that receives a light orange rating. It would also indicate that an item receiving a yellow rating would be more favorable than an item that receives a light orange rating. It would also indicate that an item receiving a light green rating would be more favorable than an item the receives a yellow rating and that an item that receives a dark green rating is more favorable than an item that receives a light green rating. It will be appreciated that in accordance with the teachings of the present invention that using colors to display the analysis of items is just one example of the numerous ways to display the analysis of items. Examples of other ways the system for analyzing items 100 can display the analysis of items includes, but is not limited to, numbers, letters, words, sounds, animations and the like.

Analysis 103, 104, 105, for example the "color ratings" illustrated in FIG. 1, is based on numerous parameters, which system for analyzing items 100 processes through numerous methods. Each method that processes and analyzes the item data is configured according to its unique purpose, each user's condition, each user's intention, each user's purpose, each user's goals, or a combination of one or more of these parameters. System for analyzing items 100 utilizes numerous methods to analyze the components of items and each method is based on a set of parameters that may or may not be adjusted by user 123. Examples of parameters and methods to process item and user data include but are not limited to health conditions and concerns such as diabetes, heart disease, cancer, allergies, and pregnancy; user preferences such as lifestyle preferences, dietary restrictions, dietary preferences, cultural preferences, and religious preferences for example, item's that qualify as fair trade, vegetarian, vegan, gluten free, low carb, low sugar, organic, non-GMO, kosher and the like; food or mineral type; an item's components such as its materials, ingredients, nutrition facts, nutrition information, availability, cost, location, inventory status, category, recall status, color, flavor, size, pattern, manufacturing information ability to be delivered, brand information, discounts, promotions, and features; location of origin of an item; material sources; an item's customer reviews; and item's inclusion in a recipe; an item or ingredient being the involved in an investigation or lawsuit; the serving size of an item; the number of times and item was purchased; the frequency of an item's purchase, the frequency of an item being searched; as well as other parameters such as meal type, comparison tools, and caloric expenditure associated with an item or ingredient. For example, a method to analyze items based on their cancer risk considers each item's carcinogen content, non-GMO verification, inflammatory ingredients and the like. In another example, for users who select the option to distinguish between which foods are favorable for a Paleo Diet and which foods are not, system for analyzing items 100 employs a method that analyzes how the combination of an item's components of items rate in terms of being in accordance with the Paleo Diet guidelines.

System for analyzing items 100 allows users to adjust individual parameters to customize methods that process item data according to the user's needs and preferences with regard to a food or mineral type. For example, a user who wants to cut down their sodium intake can adjust the "sodium" parameter the method uses to rate foods based on how high or low the food's sodium content is. System for analyzing items 100 also allows the user to select or input specific ingredients, materials, or other components that the user is either seeking out or trying to avoid helping the user identify the items that contain those components. For example, a user with a peanut allergy can input the ingredient "peanuts" as a parameter so that when the user is shopping at the store or eating at a restaurant they can use computing device 101 to identify which items were recognized as having peanuts as an ingredient and which items have been manufactured in a plant that also processes items containing peanuts. System for analyzing items 100 indicates to the user visually, audibly using audible communication device 114, or both visually and audibly, which items contain peanuts by recognizing the item and correlating it with the item's data, components, information and the like. Another example: A user who is looking for items made with 100% cotton can add "100% cotton" as a parameter for the method to consider in order to identify items that are made with 100% cotton. System for analyzing items 100 configures methods for item analysis both with and without direct user input. For example, a user who is concerned about diabetes but does not know the ingredients and components they should seek out in items and which ingredients and components to avoid can select the "Diabetes" option available through system for analyzing items 100 as an area of concern and a method configured with parameters set for users who want to avoid or manage diabetes is automatically employed for that user with system for analyzing items 100. System for analyzing items 100 includes methods to be combined or overlaid to analyze the components of items simultaneously for numerous needs or preferences with a variety of parameters. For example, a user who is managing heart disease and has a family member who only eats gluten-free items can apply both methods at the same time using system for analyzing items with methods to identify items that meet both users' needs.

The parameters set for methods used in the present invention that address health conditions and diseases can be based on medical research including direct input from a panel of medical experts in nutritional epidemiology, environmental science, oncology and chronic disease. Parameters of methods of the system for analyzing items 100 can be constantly updated and adjusted as new medical research and information or data is released about substances, materials, ingredients, etc. and as new items are introduced to the public.

System for analyzing items 100 can apply methods to configure numerous algorithms and access data from numerous databases, API's, Web and Cloud-Based Services and Platforms and through Machine Learning singularly, simultaneously, or accessing one or more of those data sources at a time.

When audible communication device 114 of system for analyzing items 100 is employed by user 123, the detection, recognition and analysis of items will be communicated audibly to user 123 by one or more sounds including but not limited to sound effects, songs, spoken words, spoken sentences and the like. For example, in FIG. 1, user 123 employs audible communication device 114 and holds computing device 101 near items 111, 112, 113. When image sensor 108 on computing device 101 detects items 111, 112, 113, user 123 hears an alert that three items have been detected. An example of such an alert is hearing three beeps indicating that three items have been detected. Continuing this example, when items 111, 112, 113 have been recognized by the system for analyzing items 100, user 123 hears another alert, for example, "Item 111, item 112 and item 113 are now being analyzed." To make the audible feature of this system for analyzing items 100 using audible communication device 114 practical for people who are blind or visually impaired, the ratings of items are presented to the user in a form that does not require vision. For instance, instead of analysis 103, 104, 105 having a color "rating," the "rating" can be expressed numerically. For example, an item can be rated on a scale of 1 to 10 with a "1 rating" indicating that an item is very unfavorable for the user and a "10 rating" indicating an item is favorable for the user. In this example, once the items are analyzed, user 123 will hear an announcement of each item's analysis. In this example, audible communication device 114 can deliver an item analysis such as "Item 111 gets a two rating. Item 112 gets a 9 rating. Item 113 gets a 1 rating." In another embodiment, audible communication device 114 can deliver an item analysis using examples of items, such as an announcement of each items' analysis for example as "Brand A Cheese Crackers gets a two rating. Brand X Egg gets a 9 rating. Brand Z Household Cleaner gets a 1 rating."

When user 123 needs clarification of what the scale is and what the numbers represent, user 123 can speak into computing device 101 to ask about the scale and what the number ratings represent and audible communication device 114 can present an audible explanation. For example, the user can speak into computing device 101 and ask, "Why did Item 111 get a 2 rating?" and system for analyzing items 100 will determine an explanation and forward the explanation to audible communication device 114. The user will receive an audible explanation through audible communication device 114 such as "Item 111 contains trans fats and the ingredient Yellow 5 which is a known carcinogen but item 111 also contains "whole wheat ingredients" which is beneficial for your health goals."

The detection, recognition, analysis and communication of that analysis can be performed in separate steps or all at once and in various ways in accordance with the teachings of the present invention.

In one embodiment, system for analyzing items 100 does not require users to capture or take pictures of items to recognize and analyze items. Users do not have to take or capture a photo of an item in order for system for analyzing items 100 to recognize the item. Simply having an item or the image of an item within the field of vision 110 of image sensor 108 of computing device 101 can activate system for analyzing items 100 to begin item analysis. Alternatively, the image of an item can be captured by computing device 101 when user 123 snaps a photo of the item using image sensor 108 and inputs that photo into system for analyzing items 100 to analyze the item, computing device 101 can recognize the item and return analysis of the item to user 123. This allows users to analyze items both in real time and at a later time when the items may not be physically near the user. System for analyzing items 100 allows the item data that corresponds to an item's captured image to be returned to the user visually, audibly or both visually and audibly.

Figure 2:
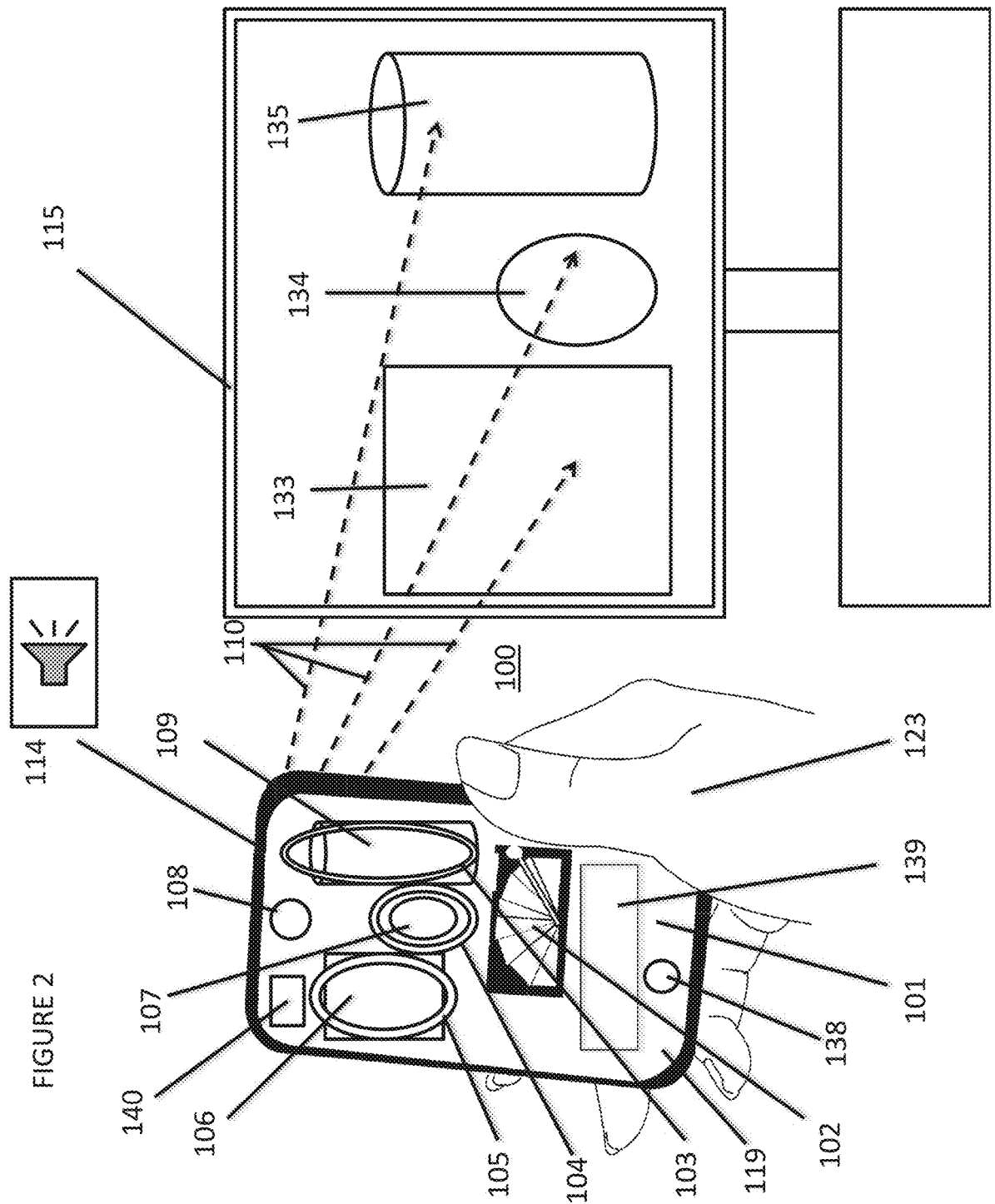
FIG. 2 is a schematic diagram of the system for analyzing items using a computing device with an image sensor to detect, recognize and analyze items in which the items are not physically present but appear as pictures of items that are displayed digitally or electronically.
Figure 3:
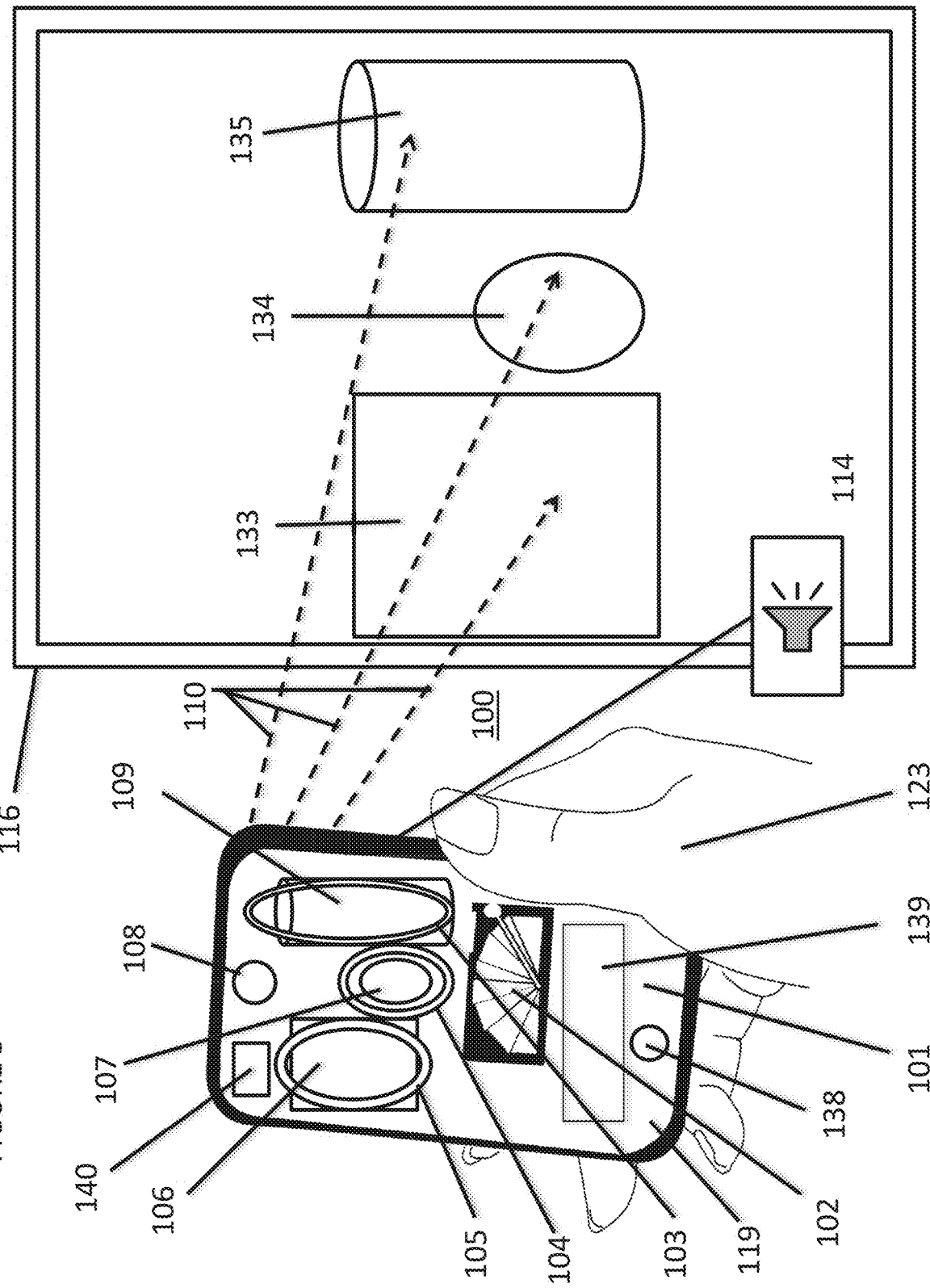
FIG. 3 is a schematic diagram of the system for analyzing items using a computing device with an image sensor to detect, recognize and analyze items in which the items are not physically present but appear as pictures of items that are displayed through another medium such as print.

Once item 111 or the image of an item 133 shown in FIGS. 2 and 3 is recognized, system for analyzing items 100 correlates the item with the item's data, processes and analyzes the item's data through numerous methods, and returns the data and analysis to the user based on the user's preferences and options selected.

FIG. 2 illustrates use of system for analyzing items 100 to analyze one or more items that are not physically present but instead, are represented in the form of an image, picture, video, or other visual display that appears on television, a computer monitor, a virtual reality device, or any other medium where images of items are displayed. In the example in FIG. 2, computing device 101 has detected and recognized image 133 of item 111 (shown in FIG. 1), image 134 of item 112 (shown in FIG. 1), and image 135 of item 113 (shown in FIG. 1) which images 133, 134 and 135 are displayed on television set 115. System for analyzing items 100 can detect, recognize, process and analyze the images of each item as if the items were physically present. System for analyzing items 100 can display image 106 of item 111, image 107 of item 112 and image 109 of item 113 on computing device 101 and return the analysis of each item 103, 104, 105 to user 123. System for analyzing items 100 can analyze actual items that are physically present and items that are not physically present but are instead represented in the form of pictures, photographs, or video such as in a commercial or advertisement. System for analyzing items 100 can detect and distinguish between all variations of items (e.g. each brand, flavor, label, version, etc.). For example, system for analyzing items 100 can analyze the differences between all the different kinds of crackers made by Brand X, Brand Y and Brand Z.

FIG. 2 illustrates an example of how user 123 receives analysis 103, 104, 105 of items 111, 112, 113. Analysis 103, 104, 105 can be communicated to user 123 in a number of ways including, but not limited to, numbers, colors, words and the like, and can be displayed by computing device 101 on display 119 as a visual display, communicated by audible communication device 114, such as a speaker or presented both visually and audibly. In the example in FIG. 1, analysis 103, 104, 105 returned to user 123 is a "rating" of each item using a color-coded system to visually display each item's "rating" to user 123. In this example, analysis 103, 104, 105 are each displayed as ratings with rings of different colors encircling images of the corresponding items displayed on computing device 101. In this example, analysis 103, 104 and 105 are rings representing the rating each item has received after system for analyzing items 100 processed components of each item. In this example, analysis 103, 104, 105 illustrates different ratings each item has received which are displayed with different colored rings around each item's image on computing device 101. In this example, analysis 105 directed to item 111 is determined by computing system 101 to have a first color rating demonstrated by a first color ring encircling image 106 of item 111 on computing device 101. For example, the first color can be orange. In this example, analysis 104 directed to item 112 is determined by computing system 101 to have a second color rating demonstrated by a second color ring encircling image 107 of item 112 on computing device 101. For example, analysis 104 directed to item 112 is determined by computing system 101 to have an egg and a second color can be green. In this example, analysis 103 directed to item 113 is determined by computing system 101 to have a third color rating demonstrated by a third color ring encircling image 109 of item 113 on computing device 101. For example, item 113 can be a household cleaner and the third color rating can be red.

System for analyzing items 100 can include color-coded scale 102 displayed on the computing device 101 to show a comparison of colors provided by analysis 103, 104, 104 to understand what each color represents in terms of each item's rating. In this example, an item receives a fourth color rating, when system for analyzing items 100 has determined that the item is a favorable item for user 123. In this example, an item receives a third color rating, when system for analyzing items 100 has determined that the item is a mostly favorable item for user 123. In this example, an item receives a second color rating, when system for analyzing items 100 has determined that the item is a mostly unfavorable item for user 123. In this example, an item receives a first color rating, when this method and system have determined that the item is very unfavorable for user 123. In this example, the various shades or hues or intensities of these colors indicate where items fall along this color-coded scale of favorable to very unfavorable by shades or hues or intensities of the corresponding colors. For example, if the color-coded scale ranges from red indicating the most unfavorable items to green as the most favorable items, a dark orange rating would indicate that an item is less favorable for user 123 than an item that receives a light orange rating. It would also indicate that an item receiving a yellow rating would be more favorable than an item that receives a light orange rating. It would also indicate that an item receiving a light green rating would be more favorable than an item the receives a yellow rating and that an item that receives a dark green rating is more favorable than an item that receives a light green rating.

It will be appreciated that in accordance with the teachings of the present invention that using colors to display the analysis of items is just one example of the numerous ways to display the analysis of items. Examples of other ways system for analyzing items 100 can display the analysis of items includes but is not limited to numbers, letters, words, sounds, animations and the like.

Analysis 103, 104, 105, for example the "color ratings" illustrated in FIG. 2 is based on numerous parameters, which system for analyzing items 100 processes through numerous methods. Each method that processes and analyzes the item data is configured according to its unique purpose, each user's condition, each user's intention, each user's purpose, each user's goals, or a combination of one or more of these parameters. System for analyzing items 100 utilizes numerous methods to analyze the components of items and each method is based on a set of parameters that may or may not be adjusted by user 123. Examples of parameters and methods to process item and user data include but are not limited to health conditions and concerns such as diabetes, heart disease, cancer, allergies, and pregnancy; user preferences such as lifestyle preferences, dietary restrictions, dietary preferences, cultural preferences, and religious preferences for example, item's that qualify as fair trade, vegetarian, vegan, gluten free, low carb, low sugar, organic, non-GMO, kosher and the like; food or mineral type; an item's components such as its materials, ingredients, nutrition facts, nutrition information, availability, cost, location, inventory status, category, recall status, color, flavor, size, pattern, manufacturing information ability to be delivered, brand information, discounts, promotions, and features; location of origin of an item; material sources; an item's customer reviews; and item's inclusion in a recipe; an item or ingredient being the involved in an investigation or lawsuit; the serving size of an item; the number of times and item was purchased; the frequency of an item's purchase, the frequency of an item being searched; as well as other parameters such as meal type, comparison tools, and caloric expenditure associated with an item or ingredient. For example, a method to analyze items based on their cancer risk considers each item's carcinogen content, non-GMO verification, inflammatory ingredients and the like. In another example, for users who select the option to distinguish between which foods are favorable for a Paleo Diet and which foods are not, system for analyzing items 100 employs a method that analyzes how the combination of an item's components of items rate in terms of being in accordance with the Paleo Diet guidelines.

System for analyzing items 100 allows users to adjust individual parameters to customize methods that process item data according to the user's needs and preferences. For example, a user who wants to cut down their sodium intake can adjust the "sodium" parameter the method uses to rate foods based on how high or low the food's sodium content is. System for analyzing items 100 also allows the user to select or input specific ingredients, materials, or other components that the user is either seeking out or trying to avoid in order to help the user identify the items that contain those components. For example, a user with a peanut allergy can input the ingredient "peanuts" as a parameter so that when the user is shopping at the store or eating at a restaurant they can use computing device 101 to identify which items were recognized as having peanuts as an ingredient and which items have been manufactured in a plant that also processes items containing peanuts. System for analyzing items 100 indicates to the user visually, audibly using audible communication device 114, or both visually and audibly, which items contain peanuts by recognizing the item and correlating it with the item's data, components, information and the like. Another example: A user who is looking for items made with 100% cotton can add "100% cotton" as a parameter for the method to consider in order to identify items that are made with 100% cotton. System for analyzing items 100 configures methods for item analysis both with and without direct user input. For example, a user who is concerned about diabetes but does not know the ingredients and components they should seek out in items and which ones to avoid can select the "Diabetes" option available through system for analyzing items 100 as an area of concern and a method configured with parameters set for users who want to avoid or manage diabetes is automatically employed for that user with system for analyzing items 100.

System for analyzing items 100 includes methods to be combined or overlaid to analyze the components of items simultaneously for numerous needs or preferences with a variety of parameters. For example, a user who is managing heart disease and has a family member who only eats gluten-free items can apply both methods at the same time using system for analyzing items with methods to identify items that meet both users' needs.

The parameters set for methods used in the present invention that address health conditions and diseases are based on medical research including direct input from a panel of medical experts in nutritional epidemiology, environmental science, oncology and chronic disease. Parameters of methods of the present invention can be constantly updated and adjusted as new medical research and information is released about substances, materials, ingredients, etc. and as new items are introduced to the public.

System for analyzing items 100 can apply methods to configure numerous algorithms and access data from numerous databases, API's, Web and Cloud-Based Services and Platforms and through Machine Learning singularly or simultaneously.

When audible communication device 114 of system for analyzing items 100 is employed by user 123, the detection, recognition and analysis of items will be communicated audibly to user 123 by one or more sounds including but not limited to sound effects, songs, spoken words, spoken sentences and the like. For example, in FIG. 2, user 123 employs audible communication device 114 and holds computing device 101 near items 111, 112, 113. When image sensor 108 on computing device 101 detects items 111, 112, 113, user 123 hears an alert that three items have been detected. An example of such an alert is hearing three beeps indicating that three items have been detected. Continuing this example, when items 111, 112, 113 have been recognized by system for analyzing items 100, user 123 hears another alert, for example, "Item 111, item 112 and item 113 are now being analyzed." To make the audible feature using audible communication device 114 system for analyzing items 100 practical for people who are blind or visually impaired, the ratings of items are presented to the user in a form that does not require vision. For instance, instead of analysis 103, 104, 105 having a color "rating", the "rating" can be expressed numerically. For example, an item can be rated on a scale of 1 to 10 with a "1 rating" indicating that an item is very unfavorable for the user and a "10 rating" indicating an item is favorable for the user. In this example, once the items are analyzed, user 123 will hear an announcement of each item's analysis. In this example, audible communication device 114 can play an item analysis such as for example "Item 111 gets a two rating. Item 112 gets a 9 rating. Item 113 gets a 1 rating." In another embodiment, audible communication device 114 can play an item analysis using examples of items, such as an announcement of each items' analysis for example as "Brand A Cheese Crackers gets a two rating. Brand X Egg gets a 9 rating. Brand Z Household Cleaner gets a 1 rating."

When user 123 needs clarification of what the scale is and what the numbers represent, user 123 speaks into computing device 101 to ask about the scale and what the number ratings represent and audible communication device 114 presents an audible explanation. For example, the user can speak into computing device 101 and ask, "Why did Item 111 get a 2 rating?" and system for analyzing items 100 will determine an explanation and forward the explanation to audible communication device 114. The user will receive an audible explanation at audible communication device 114 such as "Item 111 contains trans fats and the ingredient Yellow 5 which is a known carcinogen but item 111 also contains "whole wheat ingredients" which is beneficial for your health goals."

The detection, recognition, analysis and communication of that analysis can be performed in separate steps or all at once and in various ways in accordance with the teachings of the present invention.

In one embodiment, system for analyzing items 100 does not require users to capture or take pictures of items to recognize and analyze items, users do not have to snap a photo of an item in order to recognize the item. Simply having an item or the image of an item within the field of vision 110 of image sensor 108 of computing device 101 can activate system for analyzing items 100 to begin item analysis. Alternatively, the image of an item can be captured by computing device 101 when user 123 snaps a photo of the item using image sensor 108 and inputs that photo into system for analyzing items 100 to analyze the item, computing device 101 can recognize the item and return analysis of the item to user 123. This allows users to analyze items both in real time and at a later time when the items may not be physically near the user. System for analyzing items 100 allows the item data that corresponds to an item's captured image to be returned to the user both visually, audibly, or both visually and audibly. Once item 111 or the image of an item 133 shown in FIGS. 2 and 3 is recognized, the system for analyzing items 100 correlates the item with the item's data, processes and analyzes the item's data through numerous methods, and returns the data and analysis to the user based on the user's preferences and options selected.

FIG. 3 illustrates use of system for analyzing 100 to analyze one or more items that are not physically present but instead, are present in the form of an image, picture, video or other visual display that appear on a poster, flyer, menu, publication, or any other medium where images of items appear or are displayed. In the example in FIG. 3, computing device 101 has detected and recognized image 133 of item 111 (shown in FIG. 1), image 134 of item 112 (shown in FIG. 1), and image 135 of item 113 (shown in FIG. 1), that has appeared on poster 116. System for analyzing items 100 detects, recognizes, processes and analyzes the images of each item as if the items were physically present, displays image 106 of item 111 (shown in FIG. 1), image 107 of item 112 (shown in FIG. 1.), and image 109 of item 113 (shown in FIG. 1) on computing device 101 and returns analysis 103, 104, 105 of each respective item to user 123. System for analyzing items 100 can analyze actual items that are physically present and items that are not physically present but are instead represented in the form of pictures, photographs, or video such as in a commercial or advertisement. System for analyzing items 100 can detect and distinguish between all variations of items such as each brand, flavor, label, version and the like. For example, system for analyzing items 100 can analyze the differences between all the different kinds of crackers made by Brand X, Brand Y and Brand Z.

FIG. 3 illustrates an example of how user 123 receives analysis 103, 104, 105 of items 111, 112, 113. Analysis 103, 104, 105 can be communicated to user 123 in a number of ways including, but not limited to, numbers, colors, words and the like and can be displayed by computing device 101 on display 119 as a visual display, communicated by audible communication device 114, such as a speaker, or both displayed by a computing device 101 on display 119 as a visual display and communicated by audible communication device 114, such as a speaker.

Analysis 103, 104, 105 can be communicated to user 123 in a number of ways including but not limited to numbers, colors, words and the like and can be displayed by computing device 101 on display 119 as a visual display, communicated by audible communication device 114, such as a speaker or both displayed by computing device 101 on display 119 as a visual display and communicated by audible communication device 114, such as a speaker. In the example in FIG. 3, analysis 103, 104, 105 returned to user 123 is a "rating" of each item using a color-coded system to visually display each item's "rating" to user 123. In this example, analysis 103, 104, 105 are each displayed as ratings with rings of different colors encircling images of the corresponding items displayed on computing device 101. In this example, analysis 103, 104 and 105 are rings representing the rating each item has received after system for analyzing items 100 processed components of each item. In this example, analysis 103, 104, 105 illustrates different ratings each item has received which are displayed with different colored rings around each item's image on computing device 101. In this example, analysis 105 directed to item 111 is determined by computing system 101 to have a first color rating demonstrated by a first color ring encircling image 106 of item 111 on computing device 101. For example, the first color can be orange. In this example, analysis 104 directed to item 112 is determined by computing system 101 to have a second color rating demonstrated by a second color ring encircling image 107 of item 112 on computing device 101. For example, analysis 104 directed to item 112 is determined by computing system 101 to have an egg and a second color can be green. In this example, analysis 103 directed to item 113 is determined by computing system 101 to have a third color rating demonstrated by a third color ring encircling image 109 of item 113 on computing device 101. For example, item 113 can be a household cleaner and the third color rating can be red.

System for analyzing items 100 can include color-coded scale 102 displayed on the computing device 101 to show a comparison of colors provided by analysis 103, 104, 104 to understand what each color represents in terms of each item's rating. In this example, an item receives a fourth color rating, when system for analyzing items 100 has determined that the item is a favorable item for user 123. In this example, an item receives a third color rating, when system for analyzing items 100 has determined that the item is a mostly favorable item for user 123. In this example, an item receives a second color rating, when system for analyzing items 100 has determined that the item is a mostly unfavorable item for user 123. In this example, an item receives a first color rating, when this method and system have determined that the item is very unfavorable for user 123. In this example, the various shades or hues or intensities of these colors indicate where items fall along this color-coded scale of favorable to very unfavorable by shades or hues or intensities of the corresponding colors. For example, if the color-coded scale ranges from red indicating the most unfavorable items to green as the most favorable items, a dark orange rating would indicate that an item is less favorable for user 123 than an item that receives a light orange rating. It would also indicate that an item receiving a yellow rating would be more favorable than an item that receives a light orange rating. It would also indicate that an item receiving a light green rating would be more favorable than an item the receives a yellow rating and that an item that receives a dark green rating is more favorable than an item that receives a light green rating.

It will be appreciated that in accordance with the teachings of the present invention that using colors to display the analysis of items is just one example of the numerous ways to display the analysis of items. Examples of other ways system for analyzing items 100 can display the analysis of items includes but is not limited to numbers, letters, words, sounds, animations and the like.

Analysis 103, 104, 105, for example the "color ratings" illustrated in FIG. 2 is based on numerous parameters, which system for analyzing items 100 processes through numerous methods. Each method that processes and analyzes the item data is configured according to its unique purpose, each user's condition, each user's intention, each user's purpose, each user's goals, or a combination of one or more of these parameters. System for analyzing items 100 utilizes numerous methods to analyze the components of items and each method is based on a set of parameters that may or may not be adjusted by user 123. Examples of parameters and methods to process item and user data include but are not limited to health conditions and concerns such as diabetes, heart disease, cancer, allergies, and pregnancy; user preferences such as lifestyle preferences, dietary restrictions, dietary preferences, cultural preferences, and religious preferences for example, item's that qualify as fair trade, vegetarian, vegan, gluten free, low carb, low sugar, organic, non-GMO, kosher and the like; food or mineral type; an item's components such as its materials, ingredients, nutrition facts, nutrition information, availability, cost, location, inventory status, category, recall status, color, flavor, size, pattern, manufacturing information ability to be delivered, brand information, discounts, promotions, and features; location of origin of an item; material sources; an item's customer reviews; and item's inclusion in a recipe; an item or ingredient being the involved in an investigation or lawsuit; the serving size of an item; the number of times and item was purchased; the frequency of an item's purchase, the frequency of an item being searched; as well as other parameters such as meal type, comparison tools, and caloric expenditure associated with an item or ingredient. For example, a method to analyze items based on their cancer risk considers each item's carcinogen content, non-GMO verification, inflammatory ingredients and the like. In another example, for users who select the option to distinguish between which foods are favorable for a Paleo Diet and which foods are not, system for analyzing items 100 employs a method that analyzes how the combination of an item's components of items rate in terms of being in accordance with the Paleo Diet guidelines.

System for analyzing items 100 allows users to adjust individual parameters to customize methods that process item data according to the user's needs and preferences. For example, a user who wants to cut down their sodium intake can adjust the "sodium" parameter the method uses to rate foods based on how high or low the food's sodium content is. System for analyzing items 100 also allow the user to select and input specific ingredients, materials, or other components that the user is either seeking out or trying to avoid in order to help the user identify the items that contain those components. For example, a user with a peanut allergy can input the ingredient "peanuts" as a parameter so that when the user is shopping at the store or eating at a restaurant they can use computing device 101 to identify which items were recognized as having peanuts as an ingredient and which items have been manufactured in a plant that also processes items containing peanuts. System for analyzing items 100 indicate to the user visually and audibly using audible communication device 114, which items contain peanuts by recognizing the item and correlating it with the item's data, components, information and the like. Another example: A user who is looking for items made with 100% cotton can add "100% cotton" as a parameter for the method to consider in order to identify items that are made with 100% cotton. System for analyzing items 100 configures methods for item analysis both with and without direct user input. For example, a user who is concerned about diabetes but does not know the ingredients and components they should seek out in items and which ones to avoid can select the "Diabetes" option available through system for analyzing items 100 as an area of concern and a method configured with parameters set for users who want to avoid or manage diabetes is automatically employed for that user with system for analyzing items 100.

System for analyzing items 100 includes methods to be combined or overlaid to analyze the components of items simultaneously for numerous needs or preferences with a variety of parameters. For example, a user who is managing heart disease and has a family member who only eats gluten-free items can apply both methods at the same time using system for analyzing items 100 with methods to identify items that meet both users' needs.

The parameters set for methods used in the present invention that address health conditions and diseases are based on medical research including direct input from a panel of medical experts in nutritional epidemiology, environmental science, oncology and chronic disease. Parameters of methods of the present invention can be constantly updated and adjusted as new medical research and information or data is released about substances, materials, ingredients, etc. and as new items are introduced to the public.

System for analyzing items 100 can applying methods to configure numerous algorithms and access data from numerous databases, API's, Web and Cloud-Based Services and Platforms and through Machine Learning singularly, simultaneously, or accessing one or more of those data sources.

When audible communication device 114 of system for analyzing items 100 is employed by user 123, the detection, recognition and analysis of items will be communicated audibly to user 123 by one or more sounds including but not limited to sound effects, songs, spoken words, spoken sentences and the like. For example, in FIG. 3, user 123 employs audible communication device 114 and holds computing device 101 near items 111, 112, 113. When image sensor 108 on computing device 101 detects items 111, 112, 113, user 123 hears an alert that three items have been detected. An example of such an alert is hearing three beeps indicating that three items have been detected. Continuing this example, when items 111, 112, 113 have been recognized by system for analyzing items 100, user 123 hears another alert, for example, "Item 111, item 112 and item 113 are now being analyzed." To make the audible feature using audible communication device 114 system for analyzing items 100 practical for people who are blind or visually impaired, the ratings of items are presented to the user in a form that does not require vision. For instance, instead of analysis 103, 104, 105 having a color "rating", the "rating" can be expressed numerically. For example, an item can be rated on a scale of 1 to 10 with a "1 rating" indicating that an item is very unfavorable for the user and a "10 rating" indicating an item is favorable for the user. In this example, once the items are analyzed, user 123 will hear an announcement of each item's analysis. In this example, audible communication device 114 can play an item analysis such as for example "Item 111 gets a two rating. Item 112 gets a 9 rating. Item 113 gets a 1 rating." In another embodiment, audible communication device 114 can play an item analysis using examples of items, such as an announcement of each items' analysis for example as "Brand A Cheese Crackers gets a two rating. Brand X Egg gets a 9 rating. Brand Z Household Cleaner gets a 1 rating."

When user 123 needs clarification of what the scale is and what the numbers represent, user 123 speaks into computing device 101 to ask about the scale and what the number ratings represent and audible communication device 114 presents an audible explanation. For example, the user can speak into computing device 101 and ask, "Why did Item 111 get a 2 rating?" and system for analyzing items 100 will determine an explanation and forward the explanation to audible communication device 114. The user will receive an audible explanation at audible communication device 114 such as "Item 111 contains trans fats and the ingredient Yellow 5, which is a known carcinogen, but item 111 also contains "whole wheat ingredients," which is beneficial for your health goals."

The detection, recognition, analysis and communication of that analysis can be performed in separate steps or all at once and in various ways in accordance with the teachings of the present invention.

In one embodiment, system for analyzing items 100 does not require users to capture or take pictures of items to recognize and analyze items users do not have to snap a photo of an item in order to recognize the item. Simply having an item or the image of an item within the field of vision 110 of image sensor 108 of computing device 101 can activate system for analyzing items 100 to begin item analysis. Alternatively, the image of an item can be captured by computing device 101 when user 123 snaps a photo of the item using image sensor 108 and inputs that photo into system for analyzing items 100 to analyze the item, computing device 101 can recognize the item and return analysis of the item to user 123. This allows users to analyze items both in real time and at a later time when the items may not be physically near the user. System for analyzing items 100 allows the item data that corresponds to an item's captured image to be returned to the user both visually, audibly, or both visually and audibly. Once item 111 or the image of item 133 shown in FIGS. 2 and 3 is recognized, system for analyzing items 100 correlates the item with the item's data, processes and analyzes the item's data through numerous methods, and returns the data and analysis to the user based on the user's preferences and options selected.

Figure 4:
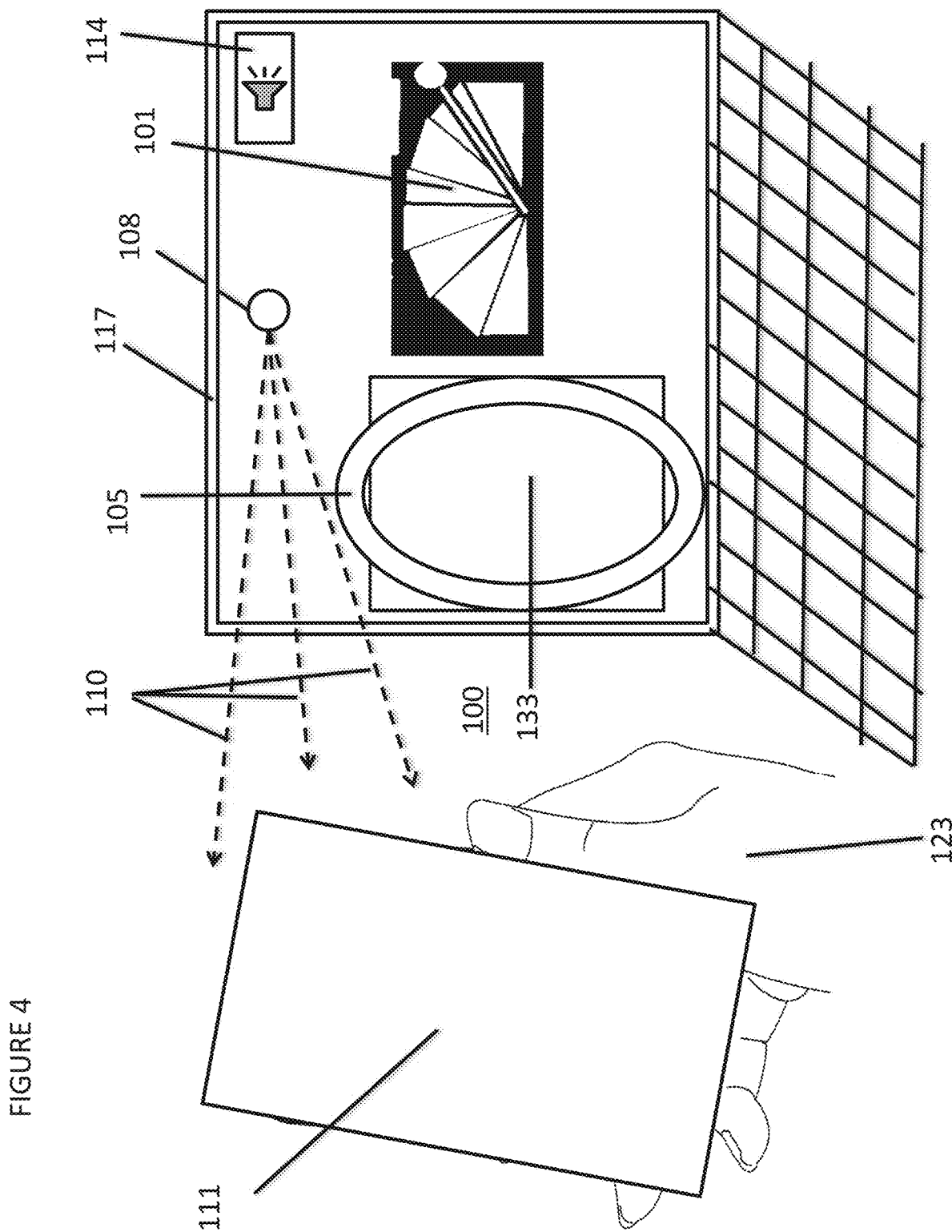
FIG. 4 is a schematic diagram of the system for analyzing items using a computing device with an image sensor to detect, recognize and analyze items using an alternate computing device with an image sensor such as a laptop to detect, recognize and analyze items and images of items.

FIG. 4 illustrates how system for analyzing items 100 can be deployed by other computing devices 101 including but not limited to computers, laptops, tablets, cell phones, smart phones, smart watches, smart glasses and the like. In the example illustrated in FIG. 4, user 123 is holding item 111 within field of vision 110 of image sensor 108 of laptop computer 117 to detect, recognize, and analyze the item. In this example, user 123 is holding item 111 that is physically present however, as explained above, user 123 can also hold images of item 133 134 135 (FIG. 3) within field of vision 110 of computing device 117 in order to receive the analysis of the item through system for analyzing items 100.

System for analyzing items 100 can detect and distinguish between all variations of items such as each brand, flavor, label, version and the like. For example, system for analyzing items 100 can analyze the differences between all the different kinds of crackers made by Brand X, Brand Y and Brand Z.

FIG. 4 illustrates an example of how user 123 receives analysis 103, 104, 105 of items 111, 112, 113. Analysis 103, 104, 105 can be communicated to user 123 in a number of ways including, but not limited to, numbers, colors, words, and the like and can be communicated by computing device 101 through a visual display, an audible communication device 114 or through both a visual display and an audible communication device 114. In the example in FIG. 3, analysis 103, 104, 105 returned to user 123 is a "rating" of each item using a color-coded system to visually display each item's "rating" to user 123. In this example, analysis 103, 104, 105 are displayed as ratings with rings of different colors encircling the images of the corresponding items that appear on the computing device 101. In this example, analysis 103, 104 and 105 are rings representing the rating each item has received after system for analyzing items 100 processed each item's components. In this example, analysis 103, 104, 105 showing different ratings each item has received are communicated by displaying different colored rings around each item's image on computing device 101. In this example, item 111 has received analysis 105 of a first color rating demonstrated by a first color ring encircling image 106 of item 111 on computing device 101. For example, the first color can be orange. In this example, item 112 has received analysis 104 of a second color rating demonstrated by a second color ring encircling image 107 of item 112 on computing device 101. For example, item 112 can be an egg and the second color can be green. In this example, item 113 has received analysis 103 of a third color rating, demonstrated by the third color ring encircling image 109 of item 113 on computing device 101. For example, item 113 can be a household cleaner and analysis 103 of the third color rating can be red.

FIG. 4 illustrates how in this example, computing device 101 system for analyzing items 100 displays on computing device 101 color-coded scale 102 to understand what each color represents in terms of each item's rating for analysis 103, 104, 105. In this example, an item receives a fourth color rating, when system for analyzing items 100 has determined that the item is a favorable item for user 123. In this example, an item receives a third color rating, when system for analyzing items 100 has determined that the item is a mostly favorable item for user 123. In this example, an item receives a second color rating, when system for analyzing items 100 has determined that the item is a mostly unfavorable item for user 123. In this example, an item receives a first color rating, when system for analyzing items 100 has determined that the item is very unfavorable for user 123. In this example, the various shades or hues or intensities of these colors indicate where items fall along the color-coded scale of favorable to very unfavorable by shades or hues or intensities of the corresponding colors. For example, if the color-coded scale ranges from red indicating the most unfavorable items to green as the most favorable items, a dark orange rating would indicate that an item is less favorable for user 123 than an item that receives a light orange rating. It would also indicate that an item receiving a yellow rating would be more favorable than an item that receives a light orange rating. It would also indicate that an item receiving a light green rating would be more favorable than an item the receives a yellow rating and that an item that receives a dark green rating is more favorable than an item that receives a light green rating.

Using colors to display the analysis of items is just one example of the numerous ways system for analyzing items 100 display the analysis of items. Examples of other ways system for analyzing items 100 can display the analysis of items includes but is not limited to numbers, letters, words, sounds, animations and the like.

Analysis 103, 104, 105 providing color ratings illustrated in FIG. 4 is based on numerous parameters, which system for analyzing items 100 processes through numerous methods. Each method that processes and analyzes the item data is configured according to its unique purpose, each user's condition, each user's intention, each user's purpose, each user's goals, or a combination of one or more of these parameters. System for analyzing items 100 utilizes numerous methods to analyze the components of items and each method is based on a set of parameters that may or may not be adjusted by user 123. Examples of parameters and methods to process item and user data include but are not limited to health conditions and concerns such as diabetes, heart disease, cancer, allergies, and pregnancy; user preferences such as lifestyle preferences, dietary restrictions, dietary preferences, cultural preferences, and religious preferences for example, item's that qualify as fair trade, vegetarian, vegan, gluten free, low carb, low sugar, organic, non-GMO, kosher and the like; food or mineral type; an item's components such as its materials, ingredients, nutrition facts, nutrition information, availability, cost, location, inventory status, category, recall status, color, flavor, size, pattern, manufacturing information ability to be delivered, brand information, discounts, promotions, and features;

location of origin of an item; material sources; an item's customer reviews; and item's inclusion in a recipe; an item or ingredient being the involved in an investigation or lawsuit; the serving size of an item; the number of times and item was purchased; the frequency of an item's purchase, the frequency of an item being searched; as well as other parameters such as meal type, comparison tools, and caloric expenditure associated with an item or ingredient. For example, a method to analyze items based on their cancer risk considers each item's carcinogen content, non-GMO verification, inflammatory ingredients and the like. In another example, for users who select the option to distinguish between which foods are favorable for a Paleo Diet and which foods are not, this system employs a method that analyzes how the combination of an item's components of items rate in terms of being in accordance with the Paleo Diet guidelines.

System for analyzing items 100 allows users to adjust individual parameters to customize methods that process item data according to needs and preferences of user 123. For example, if user 123 wants to cut down their sodium intake they can adjust the "sodium" parameter the method uses to rate foods based on how high or low the food's sodium content is. System for analyzing items 100 can allow the user to select or input specific ingredients, materials, or other components that the user is either seeking out or trying to avoid helping the user identify the items that contain those components. For example, if user 123 has a peanut allergy they can input the ingredient "peanuts" as a parameter so that when user 123 is shopping at the store or eating at a restaurant they can use computing device 101 to identify which items were recognized as having peanuts as an ingredient and which items have been manufactured in a plant that also processes items containing peanuts. System for analyzing items 100 can indicate to user 123 visually, audibly with communication device 114, or both visually and audibly, which items contain peanuts by recognizing the item and correlating it with the item's data, components, information and the like. In another example, if user 123 is looking for items made with 100% cotton they can add "100% cotton" as a parameter for a method of system for analyzing items 100 to consider in order to identify items that are made with 100% cotton. System for analyzing items 100 configures methods for item analysis both with and without direct user input. For example, if user 123 is concerned about diabetes but does not know the ingredients and components they should seek out in items and which ones to avoid they can select the "Diabetes" option available through system for analyzing items 100 as an area of concern and a method configured with parameters set for users who want to avoid or manage diabetes is automatically employed for user 123 with system for analyzing items 100.

System for analyzing items 100 can combine or overlay methods to analyze the components of items simultaneously for numerous needs or preferences with a variety of parameters. For example, if user 123 is managing heart disease and has a family member who only eats gluten-free items can apply in system for analyzing items 100 both methods at the same time to identify items that meet both users' needs.

System for analyzing items 100 can use parameters set for methods that address health conditions and diseases, which are based on medical research, including direct input from a panel of medical experts in nutritional epidemiology, environmental science, oncology and chronic disease. Parameters of methods are constantly updated and adjusted as new medical research and information or data is released about substances, materials, ingredients, and the like and as new items are introduced to the public.

System for analyzing items 100 can use methods to configure numerous algorithms and access data from numerous databases, API's, Web and Cloud-Based Services and Platforms and through Machine Learning singularly, simultaneously, or accessing one or more of those data sources.

When user 123 uses communication device 114 to provide an audible function for system for analyzing items 100, the detection, recognition and analysis of items can be communicated audibly to user 123 by one or more sounds including, but not limited to, sound effects, songs, spoken words, spoken sentences and the like. For example, in FIG. 2, user 123 employs communication device 114 and holds computing device 101 near items 111, 112, 113. When image sensor 108 of computing device 101 detects items 111, 112, 113, user 123 hears an alert that three items have been detected. An example of such an alert is hearing three beeps indicating that three items have been detected. Continuing this example, when items 111, 112, 113 have been recognized by system for analyzing items 100, user 123 hears another alert, for example, "Item 111, item 112 and item 113 are now being analyzed." To make the audible feature using audible communication device 114 of system for analyzing items 100 practical for people who are blind or visually impaired, the ratings of items are presented to the user in a form that does not require vision. For instance, instead of analysis 103, 104, 105 having a color rating, the "rating" can be expressed numerically. For example, an item can be rated on a scale of 1 to 10 with a "1 rating" indicating that an item is very unfavorable for the user and a "10 rating" indicating an item is favorable for the user. In this example, once the items are analyzed, user 123 will hear an announcement of each item's analysis. In this example audible communication device 114 of item analysis may be heard as "Item 111 gets a two rating. Item 112 gets a 9 rating. Item 113 gets a 1 rating." System for analyzing items 100 can provide audible communication device 114 with an item analysis using examples of items, user 123 could hear an announcement of each items' analysis such as "Brand A Cheese Crackers gets a two rating. Brand X Egg gets a 9 rating. Brand Z Household Cleaner gets a 1 rating."

When user 123 needs clarification of what the scale is and what the numbers represent, user 123 speaks into computing device 101 to ask about the scale and what the number ratings represent and receives an audible explanation from audible communication device 114. For example, user 123 can speak into computing device 101 and ask, "Why did Item 111 get a 2 rating?" and user 123 will receive an audible explanation from audible communication device 114 such as "Item 111 contains trans fats and the ingredient Yellow 5, which is a known carcinogen, but item 111 also contains "whole wheat ingredients," which is beneficial for your health goals."

System for analyzing items 100 can use detection, recognition, analysis and communication of that analysis can be performed in separate steps or all at once and in various ways in accordance with the teachings of the present invention.

Figure 5:
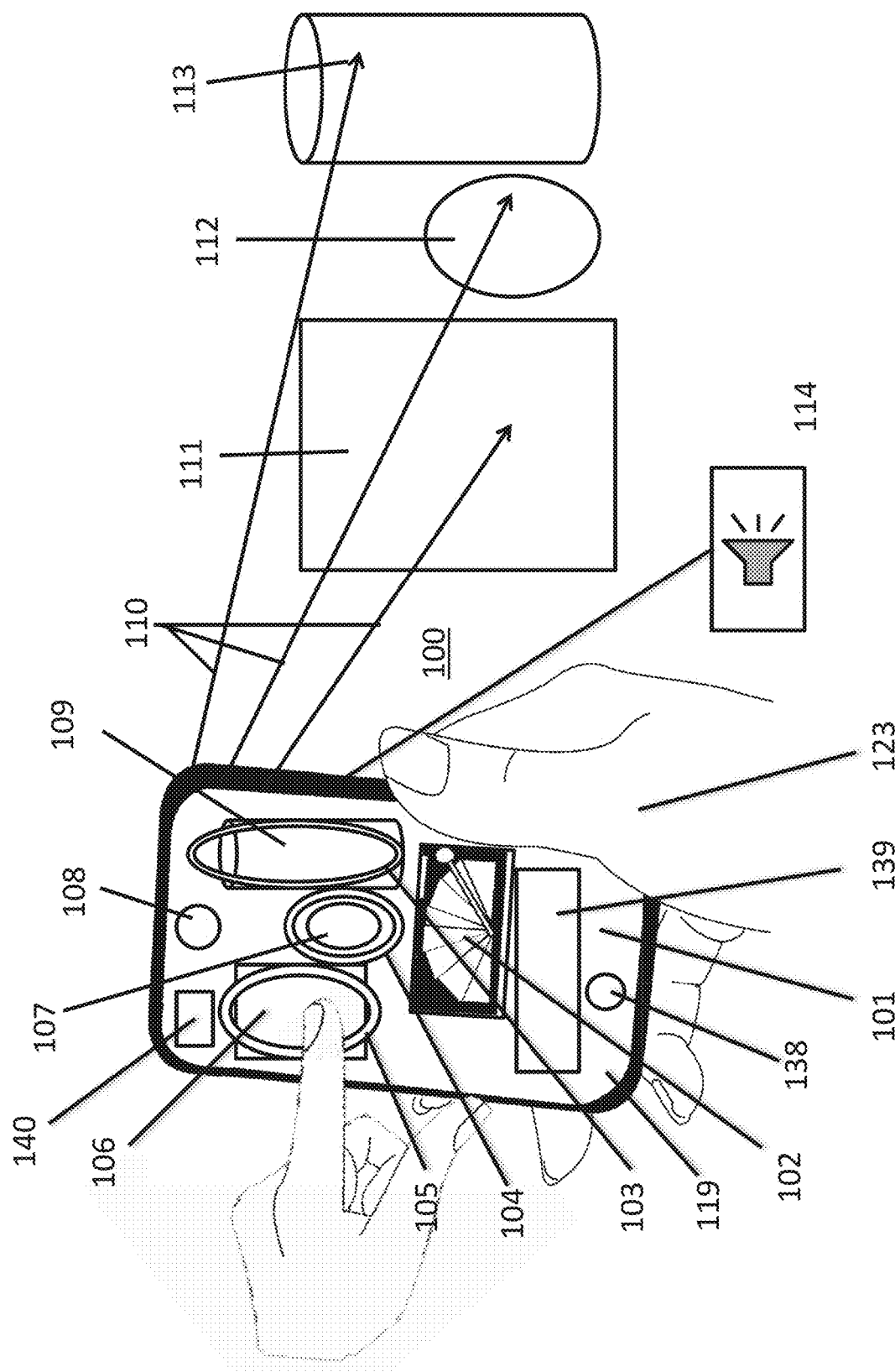
FIG. 5 is a schematic diagram showing use of the system in which a user can select the images of items that appear on a computing device once the system recognizes the items in order to receive more information or data and analysis of the items.

In one embodiment, system for analyzing items 100 does not require users to capture or take pictures of items to recognize and analyze items users do not have to take or capture a photo of an item in order to recognize the item. Simply having an item or the image of an item within the field of vision 110 of image sensor 108 of computing device 101 can activate system for analyzing items 100 to begin item analysis. Alternatively, the image of an item can be captured by computing device 101 when user 123 snaps or takes or captures a photo of the item using image sensor 108 and inputs that photo into system for analyzing items 100 to analyze the item, computing device 101 can recognize the item and return analysis of the item to user 123. This allows users to analyze items both in real time and at a later time when the items may not be physically near the user. System for analyzing items 100 allows the item data that corresponds to an item's captured image to be returned to the user both visually, audibly or both visually and audibly. Once item 111 or the image of an item 133 shown in FIGS. 2 and 3 is recognized, system for analyzing items 100 correlates the item with the item's data, processes and analyzes the item's data through numerous methods, and returns the data and analysis to the user based on the user's preferences and options selected FIG. 5 illustrates the use of system for analyzing items 100 to allow user 123 to use computing device 101 to select an image of an item on computing device 101 after it has been recognized and analyzed system for analyzing items 100 in order for user 123 to obtain more information or data about the item, obtain an explanation about the analysis of each item and execute further actions in relation to that item including, but not limited to, logging that item in a shopping list or diet log, purchasing that item from a retailer, sharing that item with another user and the like. In this example in FIG. 5, computing device 101 used by user 123 is a touch screen smart phone and user 123 is executing an action to obtain more information or data and take further action on item 111 by using a finger to touch image 106 of item 111 that appears on display 119 of computing device 101. Depending on the type of computing device 101 being used, the way a user can access more information or data and take further action on an item varies. For example, using the illustration in FIG. 4, where computing device 101 laptop 117, the act of selecting an item can be executed in a number of ways including, but not limited to, using the laptop's keyboard, mouse, touch screen, voice command feature and the like.

Figure 6:
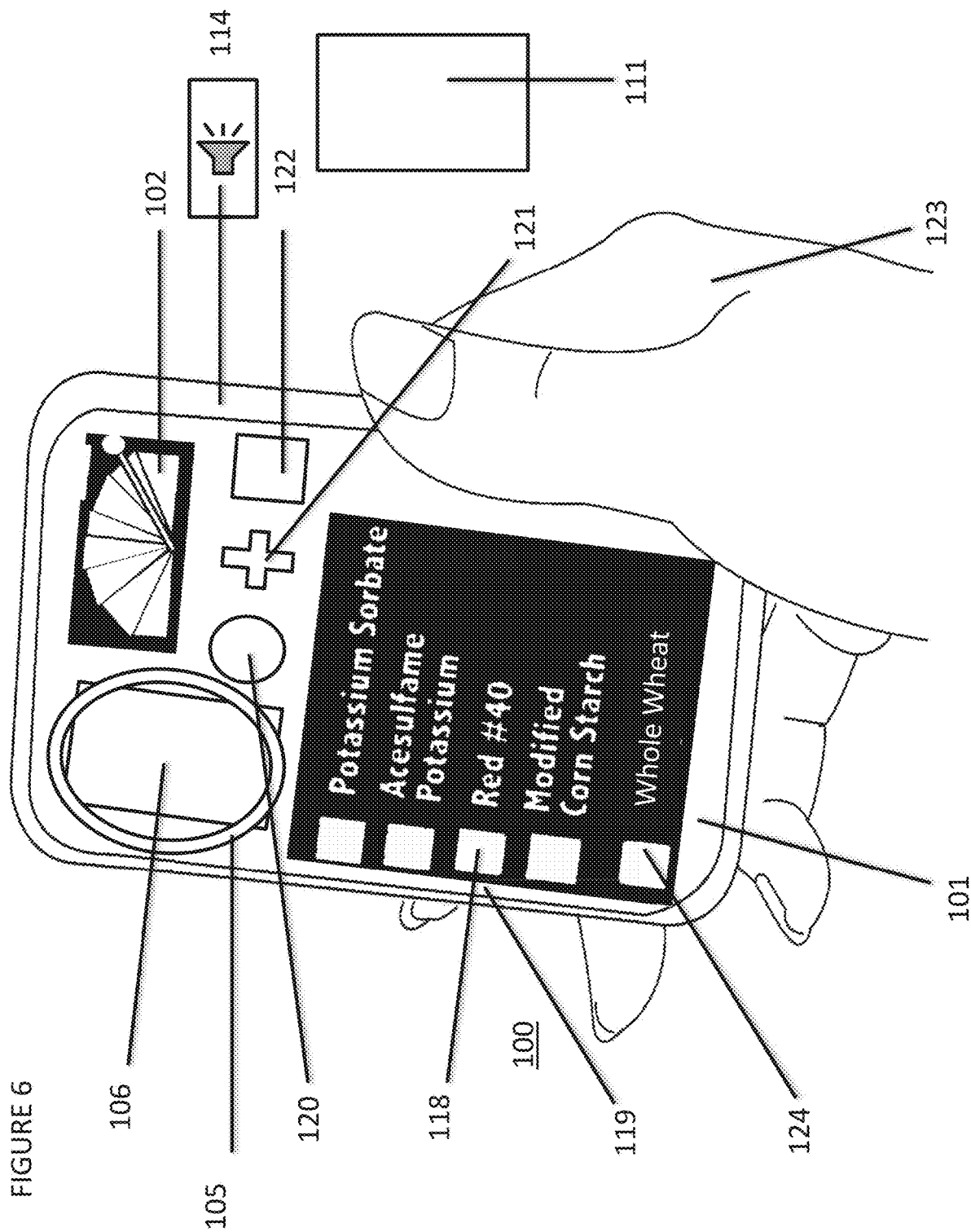
FIG. 6 is a schematic diagram showing use of the system in an example illustrating example information or data and data analysis, which a user can receive after selecting an image of an item on a computing device that has been analyzed by the system.

FIG. 6 illustrates the use of system for analyzing items 100 to allow user 123, after selecting image 106 of item 111 (FIG. 5), to access data 118 of item 111 which includes, but is not limited to, components, ingredients, nutrition information, materials, method of being processed, source, environmental impact, price, rating, availability, location and the like. System for analyzing items 100 allows user 123 to access data of an item in both a raw form or in a processed form. For example, the raw form of data of an item can include every aspect of data about the item listed in a database or every aspect of data about an item available from a manufacturer. An example of the processed form of data of an item can be ratings determined by analysis 103, 104, 105 assigned to each item as described. System for analyzing items 100 allows user 123 to access more information or data about an item to discover how the item will affect user 123.

FIG. 6 illustrates an example of information or data user 123 can receive after selecting data 118 displayed for image 106 of item 111 from analysis 105 of item 111 as shown in FIG. 5. In this example in FIG. 6, user 123 is shown the color-coded scale 102 in order to gauge a rating from analysis 105 of item 111 in terms of how favorable or unfavorable item 111 is according to the user's needs and preferences as described above with regard to FIG. 1. FIG. 6 illustrates one example of a type of information or data that is returned to user 123. In this example, user 123 is shown on display which components of item 111 contributed to an orange rating determined by analysis 105. In this example, ingredients "Potassium Sorbate," "Acesulfame Potassium," "Red 40" and "Modified Corn Starch," are displayed as unfavorable components or ingredients and ingredient "Whole Wheat" is displayed as a favorable component or ingredient of item 111.

FIG. 6 also illustrates other examples of the features users can access using system for analyzing items 100. In this example, feature 120 is displayed on display 119 to user 123 to display, for example, the serving size of an item either via audible communication or visual display 119 as described below with regard to FIG. 9. Feature 120 can also be accessed by user 123 in order to read customer reviews of items, submit customer reviews of items, share items electronically such as through social media, text, or email, purchase one or more items, and the like. System for analyzing items 100 can include add item feature 121. Add item feature 121 can be displayed on display 119 to user 123. Add item feature 121 can be used to a log or list such as a food or diet log, a shopping list, or recipe as described below with regard to FIG. 11. System for analyzing items 100 can include access to the alternative items feature 122. Access to alternative items feature 122 can be displayed on display 119 to user 123. It will be appreciated that the features described above are just a few examples of the features available through the teachings of the present invention.

System for analyzing items 100 can allow features to be accessed from one or more stages of data processing. For example, user 123 can have access to access to alternative items feature 122 shown in FIG. 11 from the initial detection and recognition phase illustrated in FIGS. 1 through 5 and phases of data displays illustrated in FIGS. 6 through 11.

Figure 7:
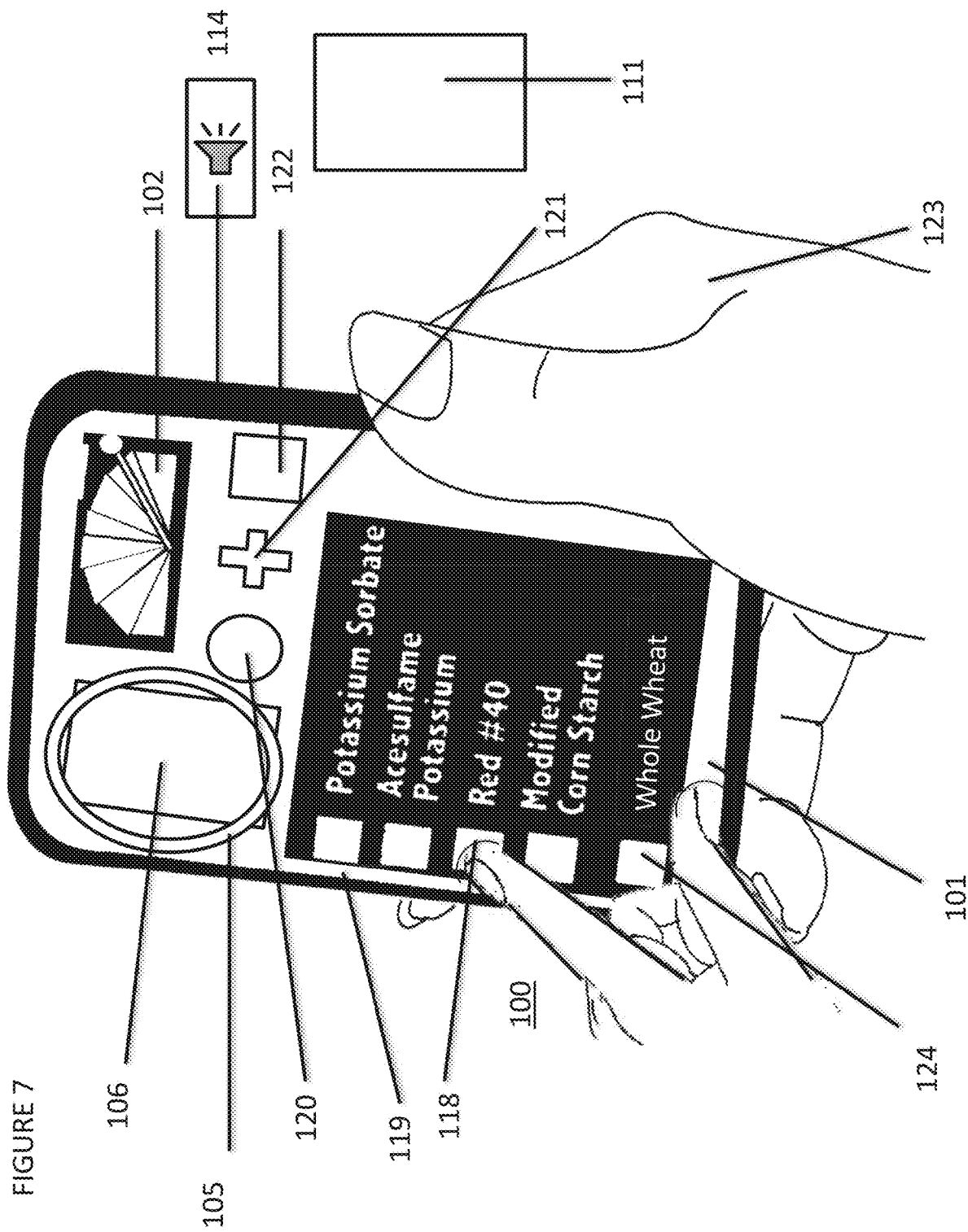
FIG. 7 is a schematic diagram showing use of the system in which a user can select an aspect of data that appears on the computing device to receive more information or data about that aspect of the data.

FIG. 7 illustrates use of system for analyzing items 100 to allow user 123 to access more information or data about the item data displayed on display 119 by selecting data 118 as the aspect of data that the user wants more information or data about. In the example in FIG. 7, user 123 uses a touch screen smart phone computing device 101 to access more information or data about the ingredient, "Red 40" by selecting data aspect 118 "Red 40" on computing device 101. Information or data about an item's components or ingredients is just one example of the type of data that user 123 can access with system for analyzing items 100. Other examples of item data 118 that can be selected by user 123 includes, but is not limited to, nutrition information, materials, method of being processed, source, environmental impact, price, rating, availability, location and the like.

Figure 8:
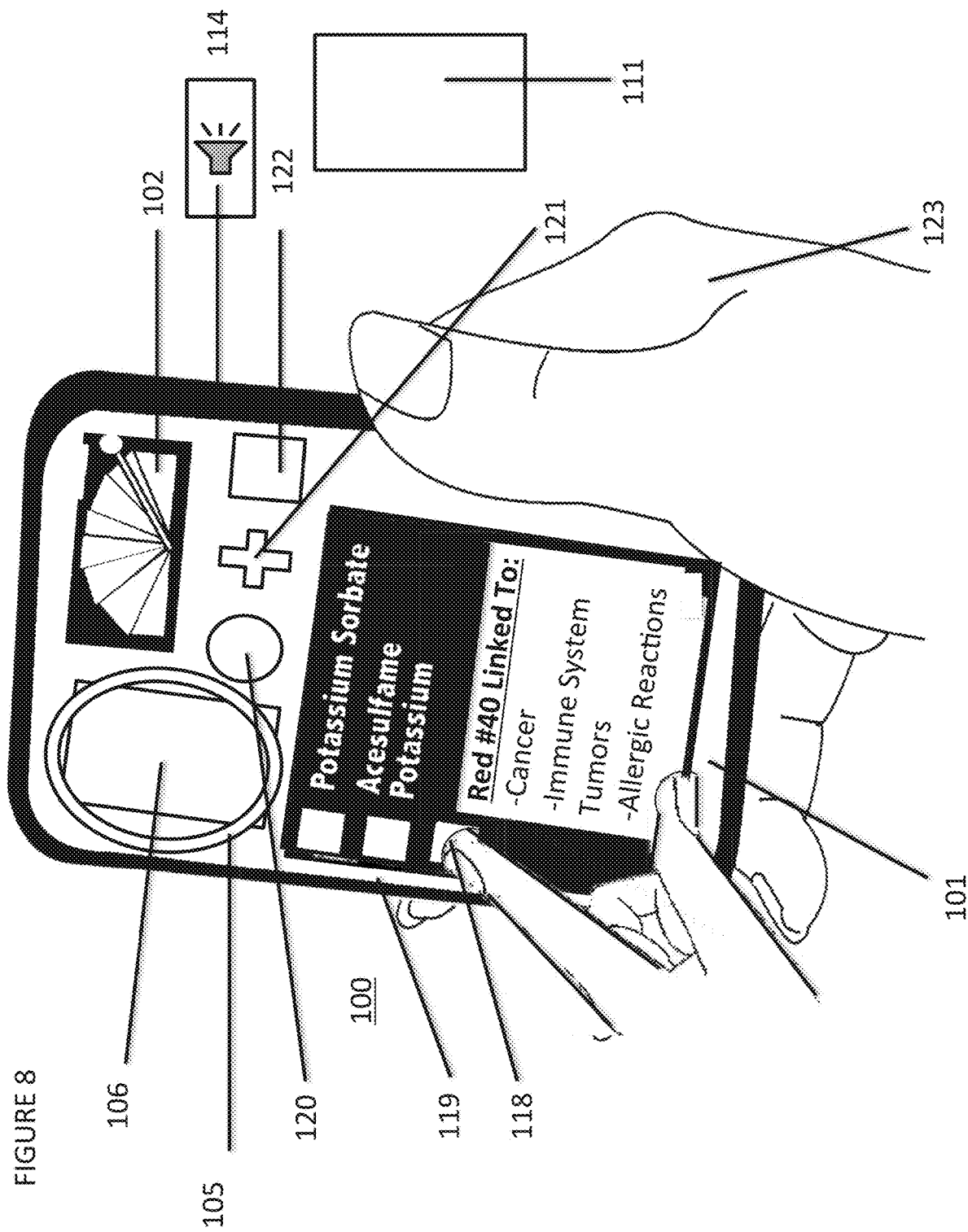
FIG. 8 is a schematic diagram showing use of the system in which example in-depth information or data is displayed to a user after the user selects an aspect of the data as shown in FIG. 7.

FIG. 8 illustrates use of system for analyzing items 100 to provide further data and explanation of item analysis. In this example, FIG. 8 illustrates information or data user 123 receives after selecting item data aspect 118, the component or ingredient "Red 40," in order to get more information or data about why "Red 40" is an unfavorable component or ingredient of item 111. In this example, system for analyzing items 100 returns to user 123 more information or data about the component "Red 40" which includes, but is not limited to, the conditions that medical research that has linked "Red 40" to which are Cancer, Immune System Tumors, ADHD, allergic reactions and the like.

It will be appreciated in accordance with the teachings of the present invention that this is one example of a type of data system for analyzing items 100 returns to user 123. Additional in-depth information or data which system for analyzing items 100 returns to user 123 includes, but is not limited to, medical studies, recipes, other users' preferences, cooking instructions and advice, shopping lists, customer reviews, investigations and lawsuits pertaining to items, each item's location, cost, availability, serving size, nutrition information, total ingredient information, location of origin, number purchased, manufacturing information, comparison tools, frequency of item searched, meal planning, exercise planning, caloric expenditure, price per unit for cost comparison, recall status, and the like.

Figure 9:
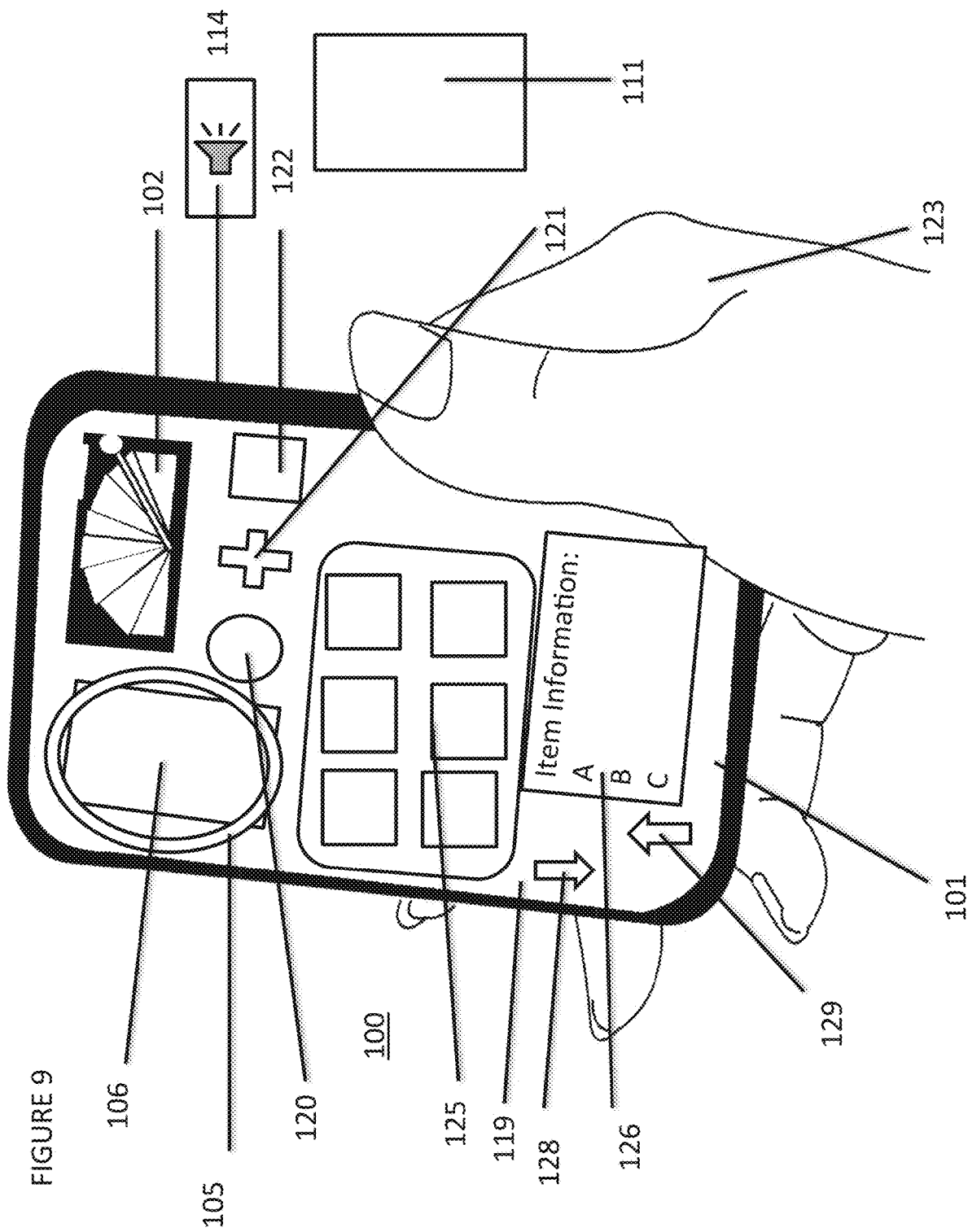
FIG. 9 is a schematic diagram showing use of the system including a visual display, and audible explanation of an item's serving size.

FIG. 9 illustrates use of system for analyzing items 100 to supply to user 123 more information or data about the item being analyzed. In the example in FIG. 9, the information or data provided is serving size 125 of the item user 123 has selected. In this example, system for analyzing items 100 returns information or data for item 111 indicating serving size 125 is six crackers and communicates nutritional information 126 in relation to serving size 125. System for analyzing items 100 provides user 123 with increase execution tool 129 to increase the number of serving sizes or decrease execution tool 128 to decrease the number of serving sizes so that the user can gauge their intake of nutritional components accordingly. For example, when user 123 chooses to use increase the number of serving sizes with increase execution tool 129 system for analyzing items can increase the number of servings from one serving to two servings. System for analyzing items 100 can calculate how an additional serving of that item impacts the user's consumption of that item in terms of its components, such as the number of calories, grams of fat, grams of sodium, grams of sugar, and displays item information or data 126 to user 123 accordingly. System for analyzing items 100 communicates to user 123 visually information or data 126, audibly using speaker or both visually and audibly 114 what the serving size of an item is and how the nutrition facts change when serving size 125 is adjusted.

Figure 10:
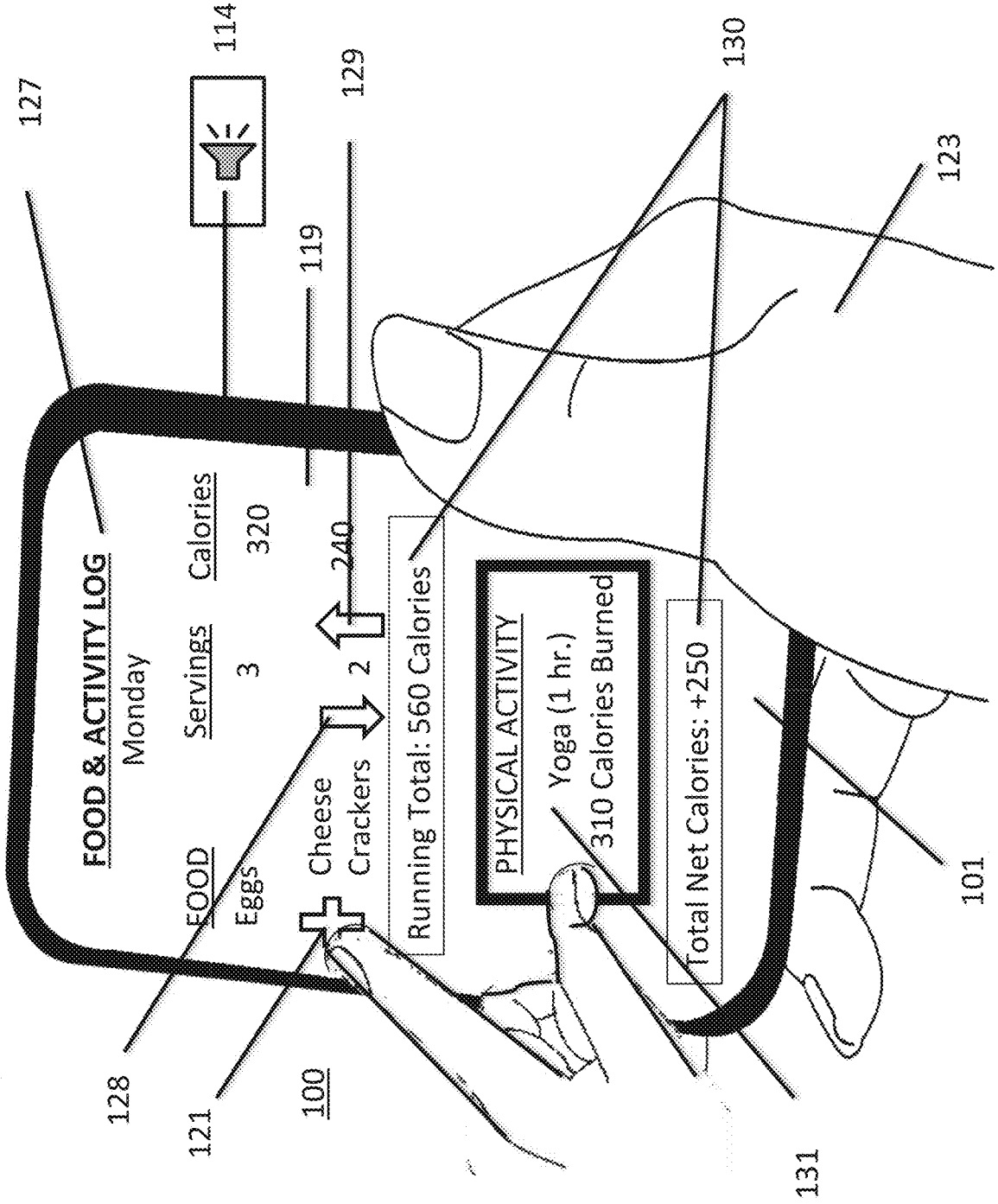

FIG. 10 illustrates use of system for analyzing items 100 to allow users to keep track of their food intake and physical activity. FIG. 10 illustrates how user 123 uses system for analyzing items 100 to detect, recognize and analyze item 111, and using add item feature 12 can add two servings of item 111 to food and activity log 127 to calculate the user's intake of nutritional components which include, but are not limited to, intake of calories, fat, sugar, sodium and the like. FIG. 10 illustrates system for analyzing items 100 allows users to adjust serving sizes according to the user's consumption in order to accurately calculate consumption using the increase execution tool 129 or decrease execution tool 128 to respectively increase or decrease the number of serving sizes so that the user can gauge their intake of nutritional components accordingly. FIG. 10 also illustrates user 123 providing input of physical activity. In this example, prior to user 123 entering input of two servings of item 111 into the food and activity log 127, user 123 inputs physical activity into physical activity feature 131, which, in this example, was a yoga class. In this example, information or data regarding the user's participation in a yoga class was also executed through image recognition. User 123 used computing device 101 to recognize the user's yoga mat, at which point user 123 was prompted to add "yoga class" to food and activity log 127 by executing add item feature 121, in order to calculate energy expenditure value 130 from calories consumed as determined in food and activity log 127 and physical activity feature 131.

FIG. 10 is an illustration to demonstrate how the data of an item can be recalled and transferred to numerous features using the image recognition and item of system for analyzing items 100. While FIG. 10 illustrates food and activity log 127 for user 123, system for analyzing items 100 allows a plurality of users to log the food intake and physical activity of numerous users at once. For example, system for analyzing items 100 allows users to keep track of their own food intake and physical activity, as well as the food intake and physical activity of others such as their family members or friends.

Figure 11:
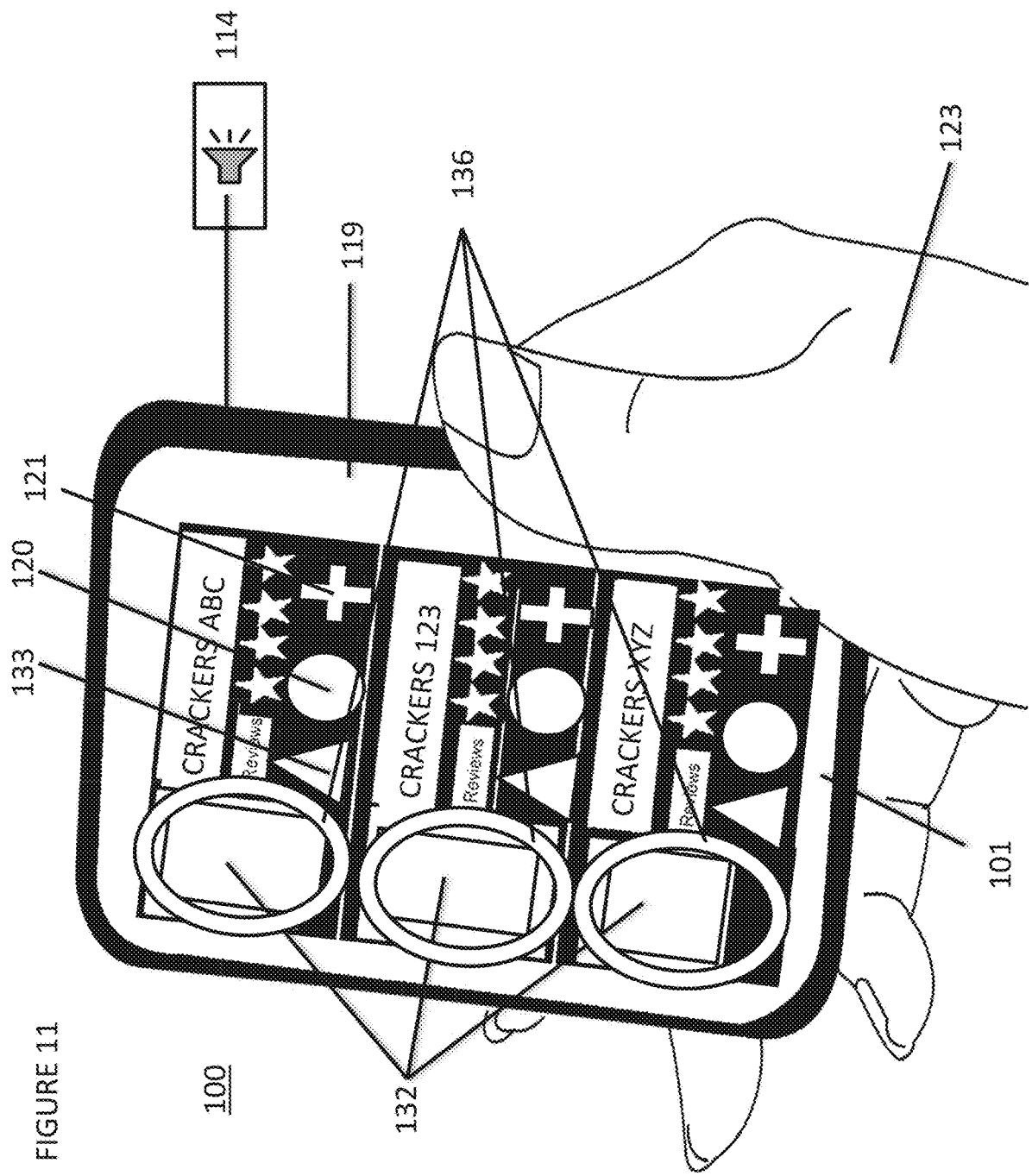
FIG. 11 is a schematic diagram of the system for analyzing items including presenting users with alternative items for consumption, purchase, analysis, and logging purposes.

FIG. 11 illustrates use of system for analyzing items 100 to supply users with information or data about alternative items 132 for purchase, consumption and analysis. This information or data regarding alternative items 132 includes, but is not limited to, alternative items' names, pictures, images, photos, ingredients, components, nutrition information, materials, method of being processed, source, environmental impact, price, rating, availability, location and the like. Alternative items 132 can either be available in the same location as user 123 For example, in the same store where user 123 is located or in a different location. For example, an item is available at another store or through an online retailer. System for analyzing items 100 allows user 123 to execute a number of actions regarding alternative items 132 displayed on display 119, voiced to the user with speaker 114, or communicated both visually and audibly to the user. Examples of the kinds of actions the user can take regarding alternative items using system for analyzing items 100 can include, but are not limited to, purchasing alternative items feature 133, accessing feature 120, which includes but is not limited to analyzing alternative items, reading customer reviews of alternative items, submitting customer reviews of alternative items, sharing alternative items electronically such as through social media, text, or email, adding alternative items to a log or list using add item feature 121 for example, a shopping list or a food or diet log, purchasing one or more items, and the like. In the example illustrated in FIG. 11, system for analyzing items 100 present user 123 with three alternative items 132 that are similar to item 111, which user 123 previously analyzed and was provided with rating 136 from analysis 105 so that the user can compare items to see which items are the most favorable for the user.

Figure 12:
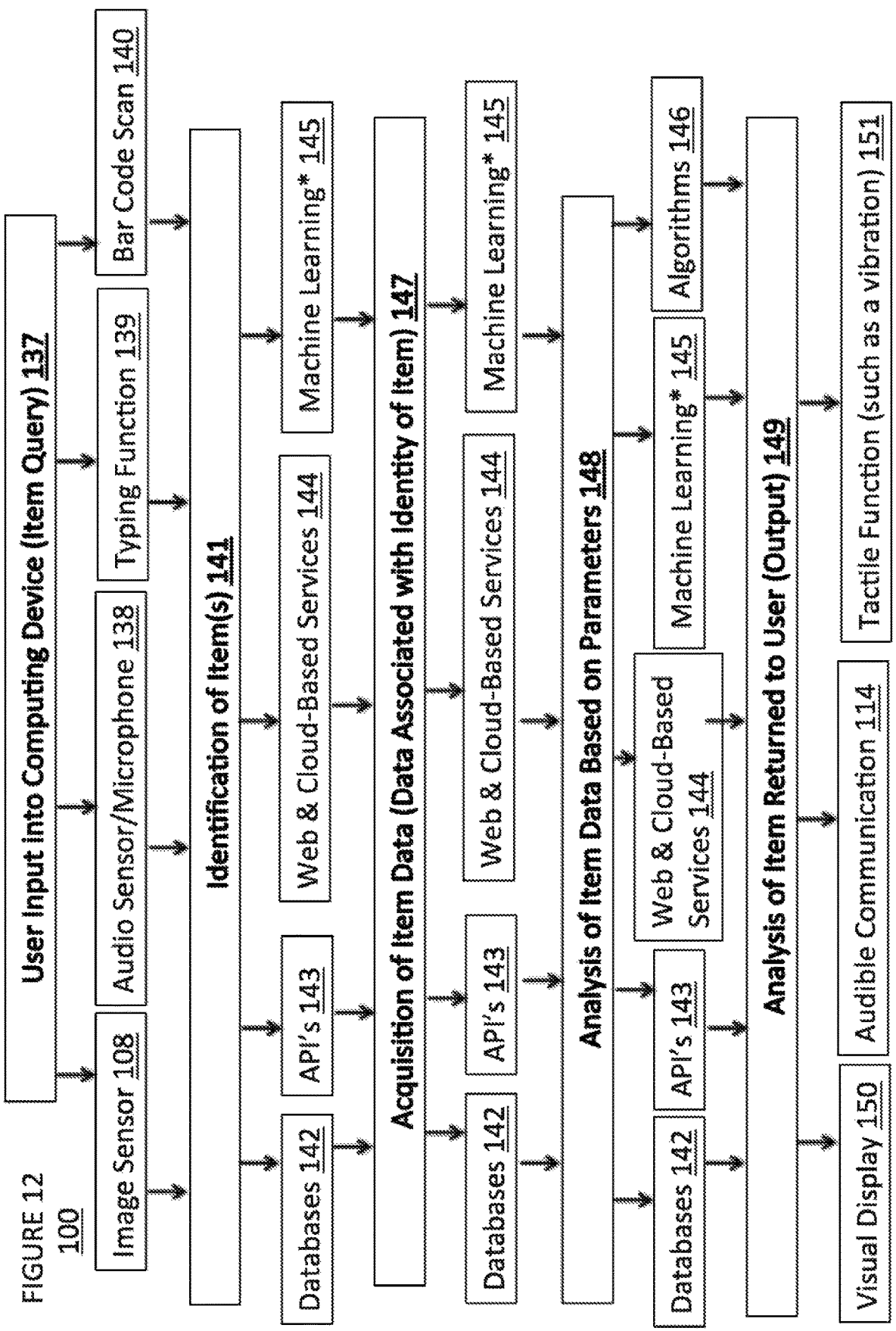
FIG. 12 is a schematic diagram of the system for analyzing items illustrating receiving input from users and delivering output to users through a user interface.

FIG. 12 illustrates a flow diagram of use of system for analyzing items 100 to receive input 137 from users and deliver output 149 to users through a user interface as shown in FIGS. 1-11. System for analyzing items 100 can receive user input 137 in multiple ways (i) using image sensor 108. For example, positioning image sensor 108 so that the field of vision of image sensor 108 includes the subject matter of the user's query. Examples of the types of subject matter a user would query using image sensor 108 include tangible items, images of items, video of items, text associated with items, and the like. (ii) using audio sensor 138 of computing device 101 such as a microphone for submitting audio data such as sounds and speech into audio sensor 138. Examples of audio data submission can include speaking a query into audio sensor 138, holding audio sensor 138 close to an audible sound and the like. (iii) using typing function 139 of computing device 101. For example, typing in the name of an item using a computing device's keyboard, or (iv) scanning using bar code scanner 140 which may be done using a specific bar code scanner or through the image sensor 108 of the computing device 101. For example, a user hovers bar code scanner 140 or image sensor 108 over an item's bar code to scan it and retrieves information or data about the item.

Once user input 137 is performed, system for analyzing items 100 launches a search to provide identification of item value 141 by processing user input 137 of an item through various data sources to match the item being queried with the item's identity. Examples of data sources used for determining identification of item value 141 can include, but are not limited to, databases 142 which can be internal and external, APIs 143, web and cloud-based services 144, and through machine learning 145. An example of use of system for analyzing items 100 to intake user input 137 and determine identification of item value 141 is a user hovering image sensor 108 of computing device 101 near a baby pacifier to find out more information about the materials used to make the baby pacifier, such as if the plastic contains BPA. To illustrate how system for analyzing items 100 differentiates between products that are similar (i.e. multiple types and brands of baby pacifiers in this example it is used "Giraffe Baby Pacifier" made by "XYZ Baby Supplies." At that point, system for analyzing items 100 can match the image of "Giraffe Baby Pacifier" made by "XYZ Baby Supplies" submitted to image sensor 108 and match it with the image of the "Giraffe Baby Pacifier" made by "XYZ Baby Supplies" that is located in database 142, allowing system for analyzing items 100 to identify the item as the "Giraffe Baby Pacifier" made by "XYZ Baby Supplies."

Once system for analyzing items 100 identifies an item, system for analyzing items 100 can acquire the corresponding item data. "Item data" is defined as information or data about the item. Examples of data sources used for this processing task of acquiring item data can include, but are not limited to, databases 142, APIs 143, web and cloud-based services 144, and through machine learning 145.

Item data acquired 147 may or may not be from the same data source that was used to initially identify the item 141. For instance, a user wants more information or item data on "Item X" that the user hears about from a friend. The user then uses audio sensor 138 of computing device 101 to submit the user input 137 to system for analyzing items 100 by speaking in the name "Item X" into audio sensor 138. System for analyzing items 100 can initially determine an identification of item value 141 for "Item X" using internal database 142 but then to acquire all the data corresponding to "Item X", system for analyzing items 100 can access multiple data sources such as API 143, a web and cloud-based service 144 or through machine learning 145 to gather different aspects of the item's data. For instance, system for analyzing items 100 can acquire the different store prices of the "Item X" from one or more API's 143 that are hosted by retailers, acquire the nutrition facts of the "Item X" from the USDA's database, and acquire information or item data about the nearest place to buy "Item X" from a cloud-based service.

Once system for analyzing items 100 acquires item data 147 from one or more data sources, system for analyzing items 100 can analyze item data through parameters set by the user. Data analysis 148 can be performed in numerous ways including, but not limited to, searching and acquiring item analysis from databases 142, API's 143, web or cloud-based services 144, through machine learning 145, by configuring and applying algorithms 146, or a combination of these actions.

An example of system for analyzing items 100 performing data analysis 148 by acquiring database information or data 142 can be when a parameter is set to rate an item as more unfavorable when an item contains carcinogens. System for analyzing items 100 can acquire data about the item's ingredients or materials from one database 142 and cross-reference that information or data with another database 142 that lists carcinogens to see if any of the ingredients or materials of the item being queried match any of the ingredients or System for analyzing items 100 performing data analysis 148 by configuring algorithm 146 is when a user, referred to as User A for example, wants to be more vigilant about lowering their sodium intake, wants to eat foods to manage their Diabetic condition, and prefers items that do not contain Palm Oil. In other words, User A makes selections so that set parameters to rate items based on how an item's nutrition facts and ingredients affect a diabetic, based on an item's sodium content and based on the presence of Palm Oil in an item. In this example, system for analyzing items 100 configures a diabetes algorithm 146 that rates or scores items based on their sugar content, glycemic index, etc. System for analyzing items 100 then adjusts algorithm 146 by increasing the coefficients related to sodium and the presence of Palm Oil in order to rate or score items according to the User A's preferences. In this example, User A uses typing function 139 of computing device 101 to submit user input 137 about "Betty Jo's Chicken Soup with Rice." System for analyzing items 100 can analyze the ingredients and nutrition facts of "Betty Jo's Chicken Soup with Rice," and return to User A a rating or score of "6" on a scale of 0 to 10 (0 being the least favorable and 10 being the most favorable) because the soup's sodium content is above User A's sodium preference of <500 mg per serving and because the soup contains Palm Oil. Whereas another user, referred to as "User B" who only selects the default "Diabetic Concern" option as user input 137 the same exact same "Betty Jo's Chicken Soup with Rice" and return to User B a rating of "8" on a scale of 1-10. "Betty Jo's Chicken Soup with Rice" gets a more favorable rating when queried by User B because the soup's sodium content and presence of Palm Oil less of a concern for User B and therefore affects the parameters that system for analyzing items 100 set to rate or score items for User B.

Algorithms 146 can have tens, hundreds or thousands of internal parameters that control the flow and performance of algorithms 146. Input and output data types for algorithms 146 are often complex and heterogeneous. Output interface 149 functions as an intermediary between the applications and the services. Output interface 149 is designed to support the applications in terms of intelligently selecting one or more of the available algorithms 146 which is capable of performing a particular task given the parameters based on, for example, the algorithms' applicable databases 142. The algorithm capabilities interface provides the applications with access to one or a combination of algorithms 146, the functional capabilities of each of algorithms 146, and a means by which to control algorithms 146 via parameters that are meaningful in terms of "real-world" characteristics rather than algorithm-centric parameters (e.g., Kosher foods or 100% cotton items). In some cases, parameters of algorithm 146 can be used to calculate application parameters, or vice versa.

System for analyzing items 100 can also perform data analysis 148 through API's 143 to translate physical or user-oriented parameters, such as the parameters to algorithm-centric parameters. APIs 143 can be used to automatically determine a set of "optimal" algorithm parameters for a particular task and parameters. The physical or user-oriented parameters can be computed by system for analyzing items 100 or) or can be specified by a user. As used herein, "optimal" may refer to, among other things, a combination of algorithm parameters that is algorithmically determined to have a high probability of performing the task according to the specified parameters, accuracy criteria, performance criteria, and other criteria. An example of system for analyzing items 100 using APIs 143 to analyze item data is collecting the prices or certification status (such as kosher or Non-GMO) of an item from multiple retailers' APIs 143 in order to return price comparison information or data to the user.

An example of system for analyzing items 100 performing item analysis through a web-based or cloud-based service includes, but is not limited to, collecting information or data from retailers on the availability of an item, such as checking store inventories. In this example, a user wants to purchase "Lotion No. 9" after system for analyzing items 100 suggested to the user that "Lotion No. 9" is one of the lotions that is highly favorable for the user based on the user's preferences and parameters. The user wants to know which stores and online retailers have "Lotion No. 9" in stock. System for analyzing items 100 can access stores' and online retailers' web based and cloud-based services 144 that provide information or data about their inventory in order to find which retailers have "Lotion No. 9" presently in stock and how many bottles of "Lotion No. 9" each retailer has in stock.

Figure 16:
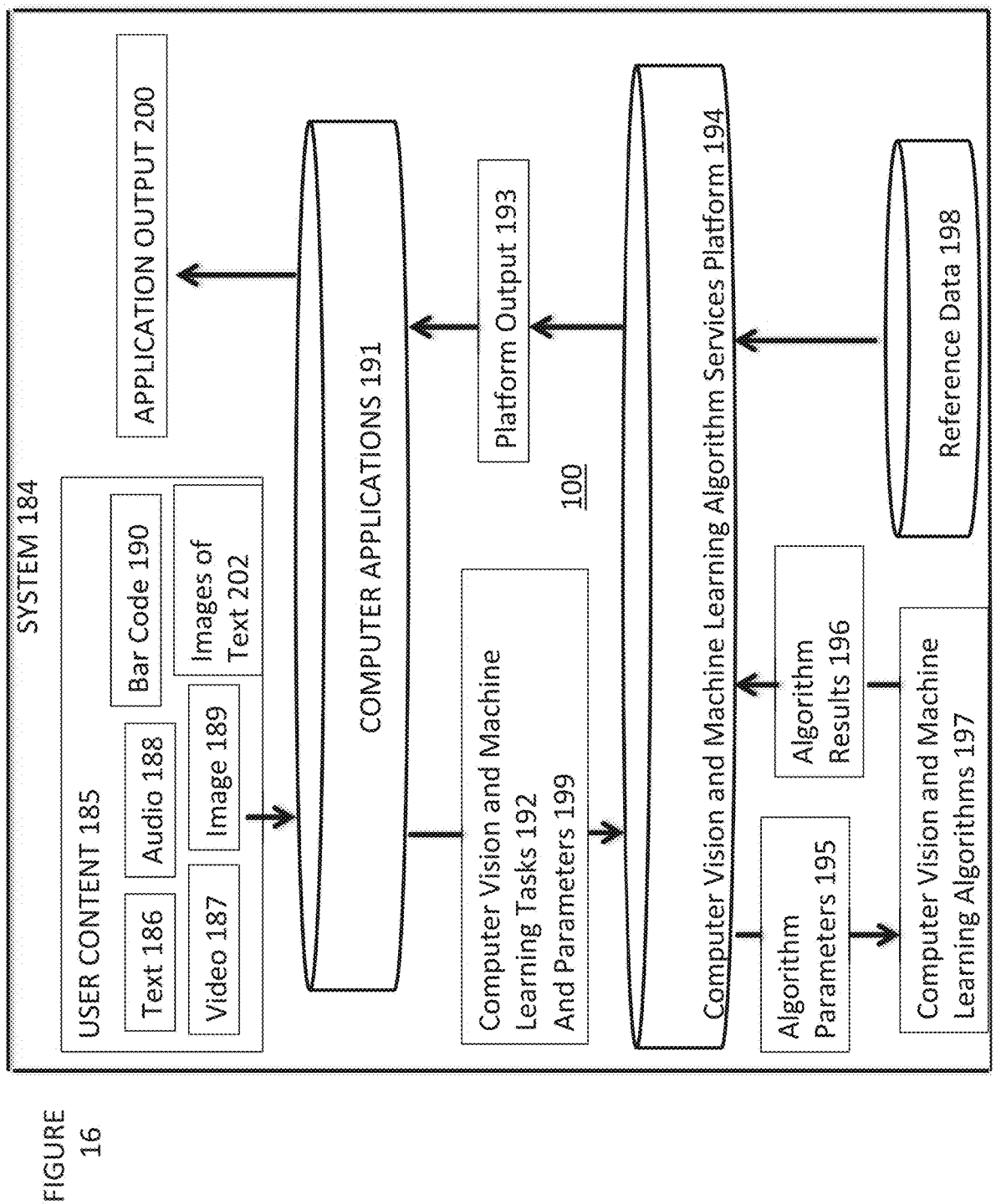
FIG. 16 is a schematic diagram of the system for analyzing items illustrating a vision and learning algorithm services platform and data processing algorithms, which are embodied in the system.

Note: The data sources of databases 142, API's 143, web or cloud-based services 144, machine learning 145, algorithms 146 at each level of data processing may include a wide variety of different content, including user content 185, as shown in FIG. 16, which can be stored in databases, files, and other electronic data stores (which may be referred to herein simply as "data" or "data sources" for ease of discussion). The data sources may include private or protected data and public or unprotected data.

Depending on the users' preferences each level of data processing 137, 141, 147, 148 within system for analyzing items 10 may or may not be apparent or accessible to the user through the user interface. For example, User C can add user input 137 and only receive returned analysis 149 whereas User D may want access to interface with the identification of items 141 to hone in on the correct item, or interface with item data acquisition process for determining item data 147 to choose their preference for where to acquire data, such as from a government database versus a corporate one or interface with data analysis 148 in terms of adjusting metrics and parameters or how the analysis is returned to the user at output interface 149. For example, whether the user prefers to see visual display 150 of the item analysis, prefers to hear audible communication of an item's analysis at speaker 114, prefers to get a tactile communication of an item's analysis such as a series of vibrations on a computing device with tactile function 151.

An example of why system for analyzing items 100 cannot be performed by a human with a pencil and paper is because it is not humanly possible to access and cross-reference the volumes of data about millions of items, as well as the volumes of data from medical research about ingredients, materials, foods etc. to configure a method in order to be able to evaluate how favorable or unfavorable items are for an individual, especially when thousands of ingredients and materials that are used to manufacture items cannot be identified by consumers. For example, the majority of consumers do not want to eat food products or use cosmetics that contain formaldehyde, but if you ask those same consumers if they eat foods or use products that contain any of the following ingredients and materials:
Imidazolidinyl urea
Diazolidinyl urea
Quaternium-15
Bronopol (2-bromo-2-nitropropane-1,3-diol)
5-Bromo-5-nitro-1,3-dioxane
Hydroxymethylglycinate
quaternium-15
DMDM hydantoin Those same consumers cannot give you a definitive answer about what those materials are or do or if they contain a substance that they do not want to consume such as formaldehyde. (Aside: all of the above ingredients and materials contain formaldehyde.)

Figure 13:
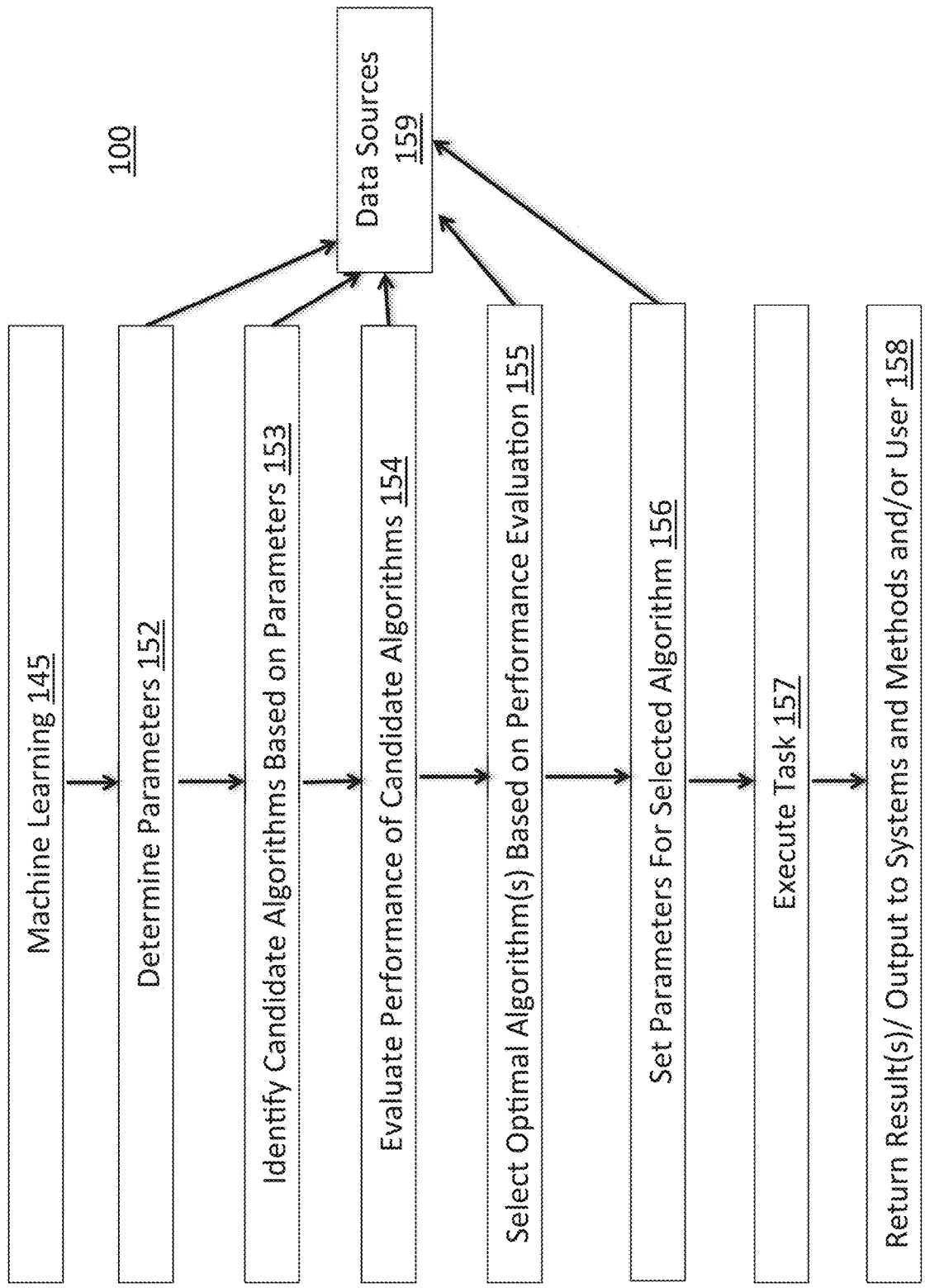
FIG. 13 is a schematic diagram of the system for analyzing items including utilizing machine learning to execute tasks.

Another example, many consumers do not want to ingest foods containing MSG so when they see "MSG" or "Monosodium Glutamate" on a label, they will choose an alternative product that does not contain MSG. However, when you ask those same consumers about whether or not the following ingredients are favorable for their health and preference, they cannot tell whether or not these ingredients are in accordance with their preferences or are favorable to their health.
Glutamic Acid
Glutamate
Monopotassium Glutamate
Calcium Glutamate
Monoammonium Glutamate
Magnesium Glutamate
Natrium Glutamate
Yeast Extract
Hydrolyzed protein
Calcium Caseinate
Sodium Caseinate
Yeast Food
Yeast Nutrient
Autolyzed Yeast
Gelatin
Textured Protein
Soy Protein Isolate
Whey Protein Isolate
Hydrolized protein FIG. 13 illustrates a flow diagram by which system for analyzing items 100 can apply computer vision or machine learning 145 to execute a task including, but not limited to, (i) identifying items 141 (ii) acquiring item data 147 and (iii) analyzing item data 148.

When system for analyzing items 100 uses computer vision and machine learning 145 to execute a task, system for analyzing items 100 then determines parameters 152 for the requested task. For example, system for analyzing items 100 can extract parameters 152 from a query string of the requested task. Then, system for analyzing items 100 can identify one or more candidate algorithms 153 to perform the requested task based on parameters 152, where the candidate algorithms 153 can comprise a subset of the library of algorithms. System for analyzing items 100 can analyze parameters 152 to determine an appropriate level of algorithm abstraction to intelligently analyze the capabilities of the candidate algorithms through machine learning 145, as described below.

Candidate algorithms 153 can be evaluated for machine learning 145. System for analyzing items 100 can evaluate the performance capabilities of candidate algorithms 154 and select one or more of optimal algorithms 155 that are optimal to perform (e.g., fully execute) the machine learning 145. System for analyzing items 100 then proceed to intelligently determine a set of parameters for the selected optimal algorithm(s) 155 in view of machine learning 145, as described below.

System for analyzing items 100 determines the optimal algorithm parameters 156 to execute optimal algorithm(s) 155 on the particular content that is the subject of machine learning 145. For example, system for analyzing items 100 can perform content-based performance characterization, wherein attributes of the content may be extracted and clustered with a dataset of previously analyzed content, to identify optimal algorithm parameters 156. System for analyzing items 100 then proceeds to execute a task of machine learning 145 using parameters 156, as described below.

System for analyzing items 100 executes a task of machine learning 145 using the selected optimal algorithms 155 and optimal algorithm parameters 156 and obtain algorithm results 158. System for analyzing items 100 can initiate the executing of the algorithms through one or more APIs. System for analyzing items 100 then communicates algorithm results 158 of performing a task of machine learning 145 with the selected optimal algorithms 155 as output 158 for use by system for analyzing items 100 for further functions and to the user directly either visually, audibly or through a tactile function of computing device 101.

For example, when system for analyzing items 100 chooses to identify 141 an item using machine learning 145, the identity of that item can be returned back to system for analyzing items 100 for the following step of acquiring data 147 associated with that item, or system for analyzing items 100 can return the identity of that item directly to the user through an interface so that the user can verify that the identity of the item is accurate before system for analyzing items 100 proceeds to acquire item data 147, analyze item data 148, etc.

In some embodiments, the task 145 involves applying one or more computer vision or machine learning algorithms to the user input and information or data and returning result 158 of the algorithm execution to system for analyzing items 100. Alternatively, or in addition, task 145 can include a request to select an appropriate algorithm 155 for use in processing particular input and a request to determine an appropriate set of parameters 152, 156 to use with a particular algorithm in processing certain data.

Based on task 145 and one or more parameters 152 relating to task 145 (which may be supplied to system for analyzing items 100 as part of the task 145 or separately from the task 145), system for analyzing items 100 can select one or more of the computer vision or machine learning algorithms to perform task 145. System for analyzing items 100 can access data sources 159 in order to inform its algorithm selection process and to perform the requested task 145. For instance, the system for analyzing items 100 can utilize data sources 159 to characterize and predict the capabilities of one or more of the algorithms in relation to the particular task 145. System for analyzing items 100 can execute the selected algorithm(s) 155 to perform the task 145 with the requisite algorithm parameters 156, receive algorithm results 158 (e.g., the output of the execution of the selected algorithm 155), and returns the output 158 (e.g., the algorithm results and an "application friendly" version of the algorithm results) for use by system for analyzing items 100.

In turn, system for analyzing items 100 can process the output 158 according to the needs of system for analyzing items 100 and, as a result, present additional output 149. The selected algorithm(s) 155 perform the task 145 by, for instance, algorithmically extracting useful information or data from the images and comparing the useful information or data for each of the images to a portion of the data sources 159. System for analyzing items 100 can supply the matching images or data relating to the matching images (such as the name of each item recognized in each of the images, or a computer storage location at which the matching images can be accessed) to system for analyzing items 100 as output 158. System for analyzing items 100 can formulate output 158 for presentation to an end user. For instance, system for analyzing items 100 can place the recognized items' names and scores on or adjacent to each image and display the image and recognized name on a display device of a computing device as illustrated in FIGS. 1 through 11 or system for analyzing items can invoke a text-to-speech processor to output the recognized items' names and scores as machine-generated speech audio 114. Alternatively, or in addition, system for analyzing items 100 can use the identity of an item for a subsequent task, such as to log an item in a diet log or a shopping list or to query other information or data relating to the user. The manner in which system for analyzing items 100 ultimately utilize the output of computer vision and machine learning algorithms 145 can vary depending on the requirements or design of the tasks requested of system for analyzing items 100.

Some embodiments of system for analyzing items 100 can be implemented as an application programming interface (API) or as a collection of APIs, which is made available to applications (or application developers) as an Internet-based service (e.g., a web service).

Figure 14:
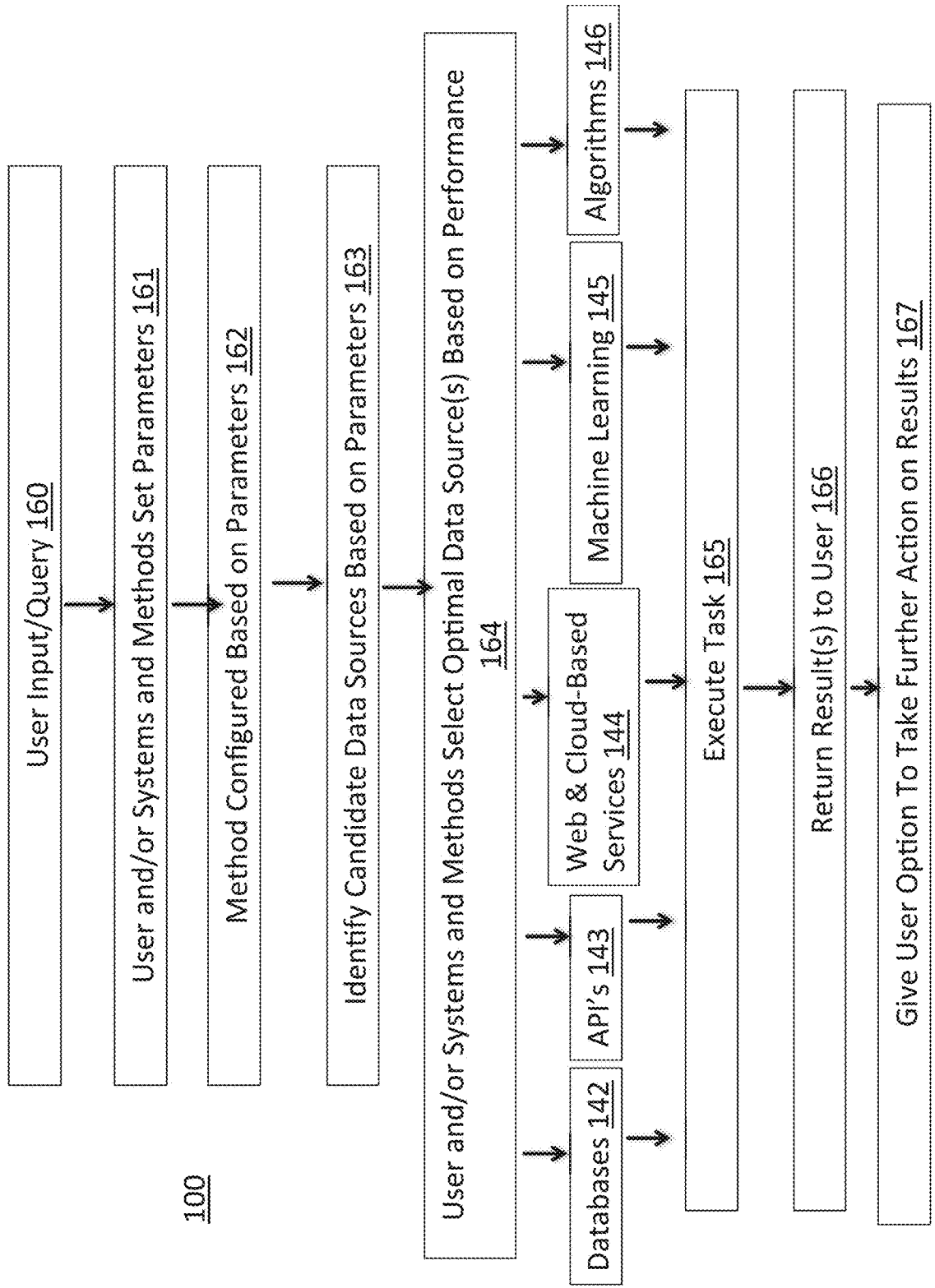
FIG. 14 is a schematic diagram of the system for analyzing items including utilizing searching, processing and retrieving metadata.

FIG. 14 illustrates how this system for analyzing items 100 can allow users to take an active role in searching, processing and retrieving metadata. The process illustrated in FIG. 14 closely resembles the process in FIG. 13 however the distinction is this: The process in FIG. 13 is one of machine learning so system for analyzing items 100 are executing tasks (e.g., configuring and selecting algorithms, setting parameters) predominantly on their own accord (i.e. without the user). Whereas the process illustrated in FIG. 14 allows the user to take an active role in executing tasks (e.g., configuring and selecting algorithms, setting parameters) throughout the process. Another difference between the process illustrated in FIG. 13 versus the process illustrated in FIG. 14 is that the process illustrated in FIG. 13 is a subsystem that can be accessed by system for analyzing items 100 to complete the process illustrated in FIG. 12. For example, system for analyzing items 100 can use machine learning (FIG. 12, 14) to identify an item (FIG. 12, 141). Whereas the process illustrated in FIG. 14 is not a subsystem within the process illustrated in FIG. 12. The process illustrated in FIG. 14 is an additional function of system for analyzing items 100 in conjunction with or separately from the function illustrated in FIG. 12.

For the purposes of clarity, we will describe the process illustrated by FIG. 14 with tangible examples. However, these examples are only for illustrative purposes and do not encompass the entirety of the usage of the function illustrated in FIG. 14.

The process illustrated in FIG. 14 begins with user input 160. Input 160 may or may not be the user output 149 from the process illustrated in FIG. 12 (i.e. a secondary action taken on the user output 149). An example of user input 160 as a secondary action taken on user output 149 is when a user is returned as a list of alternative items as output 149 as described in FIG. 11. The user can then take secondary action on that output 149 by, for instance, launching a secondary query 160 on an item that was identified 141 and analyzed 149 through the process illustrated in FIG. 12 through system for analyzing items 100. This query 160 for example may include, but is not limited to, asking system for analyzing items 100 where these alternative items can be found, where these alternative items can be purchased, the various prices of these alternative items by retailer and location, the rating or score of these alternative items, etc. Using this example, these queries 160 may be singular in nature (e.g. location of items only) or multi-faceted in nature (e.g. where these alternative items can be found, where these alternative items can be purchased, the various prices of these alternative items by retailer and location, the rating or score of these alternative items all at the same time).

Depending on the user's preferences, the user can take direct action and control as to which queries to input 160 thereby actively setting parameters 161 system for analyzing items 100 can set parameters 161 without the user or the parameters 161 can be set by both the user and system for analyzing items 100. For example, a user can provide input 160 as a query to system for analyzing items 100 for the location of an item by actively setting "location" as a parameter 161 while system for analyzing items 100 will set parameter 161 of "within a 5-mile radius of the user's current location" without the user making any active adjustments. Note: However, using this example, the user can adjust the parameter 161 of "within a 5-mile radius of the user's current location" to another setting such as the parameter 161 of "within a 10-mile radius of the user's home address."

Examples of parameters include, but are not limited to, health conditions and concerns such as diabetes, heart disease, cancer, allergies, and pregnancy, as well as lifestyle preferences (e.g., fair trade, vegetarian, vegan, gluten free, low carb, low sugar, organic, non-GMO, kosher, etc.), medical studies, recipes, other users' preferences, cooking instructions and advice, shopping lists, customer reviews, investigations and lawsuits pertaining to items, as well as each item's location, cost, availability, serving size, nutrition information, total ingredient information, location of origin, number purchased, manufacturing information, comparison tools, frequency of item searched, meal planning, exercise planning, caloric expenditure, price per unit for cost comparison, recall status, and the like.

Once this system and method for analyzing items 100 receive the user's input 160 and parameters 161 are established, this system for analyzing items 100 will configure a method based on the parameters 161 that are set. This system and method for analyzing items will then identify which data sources 142, 143, 144, 145, 146 contain the data needed to execute the task 165 (i.e. which data source(s) 142, 143, 144, 145, 146 contain the information or data the user is looking for or has queried the system for analyzing items 100 for). Data sources 142, 143, 144, 145, 146 can include but are not limited to databases 142, API's 143, web or cloud-based services or platforms 144, machine learning 145, etc. and can be used singularly or in conjunction with each other.

Based on the user's preferences, the user can allow system for analyzing items 100 to choose the optimal data source 142, 143, 144, 145, 146 164 and execute the task 165 or the user can actively select the data source 142, 143, 144, 145, 146 that the user thinks is optimal 164 to execute the task 165 based on the options of data source(s) 142, 143, 144, 145, 146 available for system for analyzing items 100 to execute the task 165. For example, a user who has conducted several queries 160 and prefers the results that have been returned to the user when system for analyzing items 100 use databases 142 versus API's 143 may, at this step in the process, select databases 142 as the data source 142, 143, 144, 145, 146 to execute this task 165.

System for analyzing items 100 also allow the user to set their data source 142, 143, 144, 145, 146 preferences as part of the set of parameters 162 available to the user. System for analyzing items 100 will then execute the task 165 and return the results or data 166 to the user at which point the user can then take further action 167 including, but not limited to, purchasing an item, logging an item in a food log or activity log or shopping list, asking for more information or data about an item, etc. as illustrated in FIGS. 6 through 11.

Another example of the function illustrated in FIG. 14 is when input 160 is inputted by a medical researcher. System for analyzing items 100 allows users to use a computing device to submit to system for analyzing items 100 their medical history, health conditions, issues, and the like. Continuing this example, system for analyzing items 100 allowed users to log or keep track of when their migraines occur. Continuing this example as it relates to the illustration in FIG. 14, input 160 can be, for instance, "migraine log"+"food and activity log" in order to see—by aggregating the data of millions of users—if any correlations can be made between certain foods and activities that may contribute to migraine headaches or prevent migraine headaches. For example, after aggregating the data, the medical researcher notices a strong correlation between users who eat Brie cheese and suffer migraines shortly after eating the Brie cheese and can conduct further medical research to see which components of Brie cheese could trigger a migraine headache.

In this example, the medical researcher has selected specific parameters 161 for system for analyzing items 100 to configure a method 162 based on the parameters 161 that are set. System for analyzing items 100 can then identify which data source(s) 142, 143, 144, 145, 146 contain the data needed to execute the task (i.e. which data source(s) 142, 143, 144, 145, 146 contain the information or data the medical researcher is looking for or has queried system for analyzing items 100 for). Data sources 142, 143, 144, 145, 146 can include but are not limited to databases 142, API's 143, web or cloud-based services or platforms 144, machine learning 145, etc. and can be used singularly or in conjunction with each other.

Based on the medical researcher's preferences, the medical researcher can allow system for analyzing items 100 to choose the optimal data source 142, 143, 144, 145, 146 and execute task 165 or the medical researcher can actively select the data source 142, 143, 144, 145, 146 that the medical researcher thinks is optimal 164 to execute the task 165 based on the options of data sources 142, 143, 144, 145, 146 of system for analyzing items 100 have provided to the medical researcher. For example, a medical researcher who has conducted several queries 160 and prefers the results 166 that have been returned to the medical researcher when system for analyzing items 100 used a web-based service 144 versus a local database 142. At this step in the process, the medical researcher can select the web-based service 144 as the data source for system for analyzing items 100 to execute this task.

System for analyzing items 100 can then execute task 165 and return results or data 166 to the medical researcher at which point the medical researcher can then take further action 167. For example, system for analyzing items 100 return to the medical researcher data that shows a correlation between users who logged "Brie Cheese" regularly in their diet log and suffered migraines. The medical researcher could perform a secondary query of input 160 to see if there were correlations of other conditions or allergies among users who logged "Brie Cheese" in their diet log.

Another example of how system for analyzing items 100 can be used is illustrated in FIG. 14 as by a government entity during an outbreak such as the *e-coli* outbreak in 2006 where 3 people died, 31 people suffered kidney failure and almost 200 people were infected after eating organic spinach that came from a specific farm. The spinach was distributed to stores across the country and the *e-coli* infections were scattered throughout the country making it difficult to locate the source of the problem quickly and warn consumers to limit the number of infections.

Referring to FIG. 14, by submitting query 160, a government entity can access the data of users who have logged their food intake and have submitted input that they have experienced a sudden illness or infection or specifically *e-coli* by setting these as parameters 161 for their query 160. Using system for analyzing items 100, that data can also be cross-referenced with users' shopping list, shopping cart, and item search history by a researcher or government entity to find the correlation between users' who were infected and their consumption of specific products in order to narrow down the specific product containing the contaminant and the location where the product was sourced. In reference to FIG. 14, a government entity inputs a query 160 with parameters 161 such as "*e-coli*"+"Food Log"+"Shopping History." System for analyzing items 100 can then configure a method 162 based on those parameters 161.

This system for analyzing items 100 then identify which data source 142, 143, 144, 145, 146 contain the data needed to execute the task (i.e. which data source 142, 143, 144, 145, 146 contain the information or data the government entity is looking for or has queried the system for analyzing items 100 for). Data sources 142, 143, 144, 145, 146 can include but are not limited to databases 142, API's 143, web or cloud-based services or platforms 144, machine learning 145, and the like and can be used singularly or in conjunction with each other.

Based on the government entity's preferences, the government entity can allow system for analyzing items 100 to choose the optimal data source 142, 143, 144, 145, 146 and execute the task 165 or the government entity can actively select the data source 142, 143, 144, 145, 146 that the government entity thinks is optimal 164 to execute the task 165 based on the options of data sources 142, 143, 144, 145, 146 system for analyzing items 100 have provided to the government entity. For example, a government entity who has conducted several queries 160 and prefers the results 166 that have been returned to the government entity when system for analyzing items 100 access APIs 143 and databases 142 versus machine learning 145. At this step in the process, the government entity can select APIs 143 and databases 142 as the data sources for system for analyzing items 100 to execute this task.

System for analyzing items 100 will then execute task 165 and return results or data 166 to the government entity at which point the government entity can then take further action 167. For example, system for analyzing items 100 will return to the government entity data that shows a correlation between users who logged "raw spinach" regularly in their diet log, had "Sunshine Farm Bagged Spinach" in their shopping history and suffered an *e-coli* infection. An example of secondary action 167 the government entity could take at that point is to use system for analyzing items 100 to issue an alert or warning about the possible correlation between *e-coli* and "Sunshine Farm Bagged Spinach" to all users of system for analyzing items 100. By alerting consumers quickly on a massive scale, system for analyzing items 100 can be used to reduce the number of deaths and serious health consequences of outbreaks such as this one.

Figure 15:
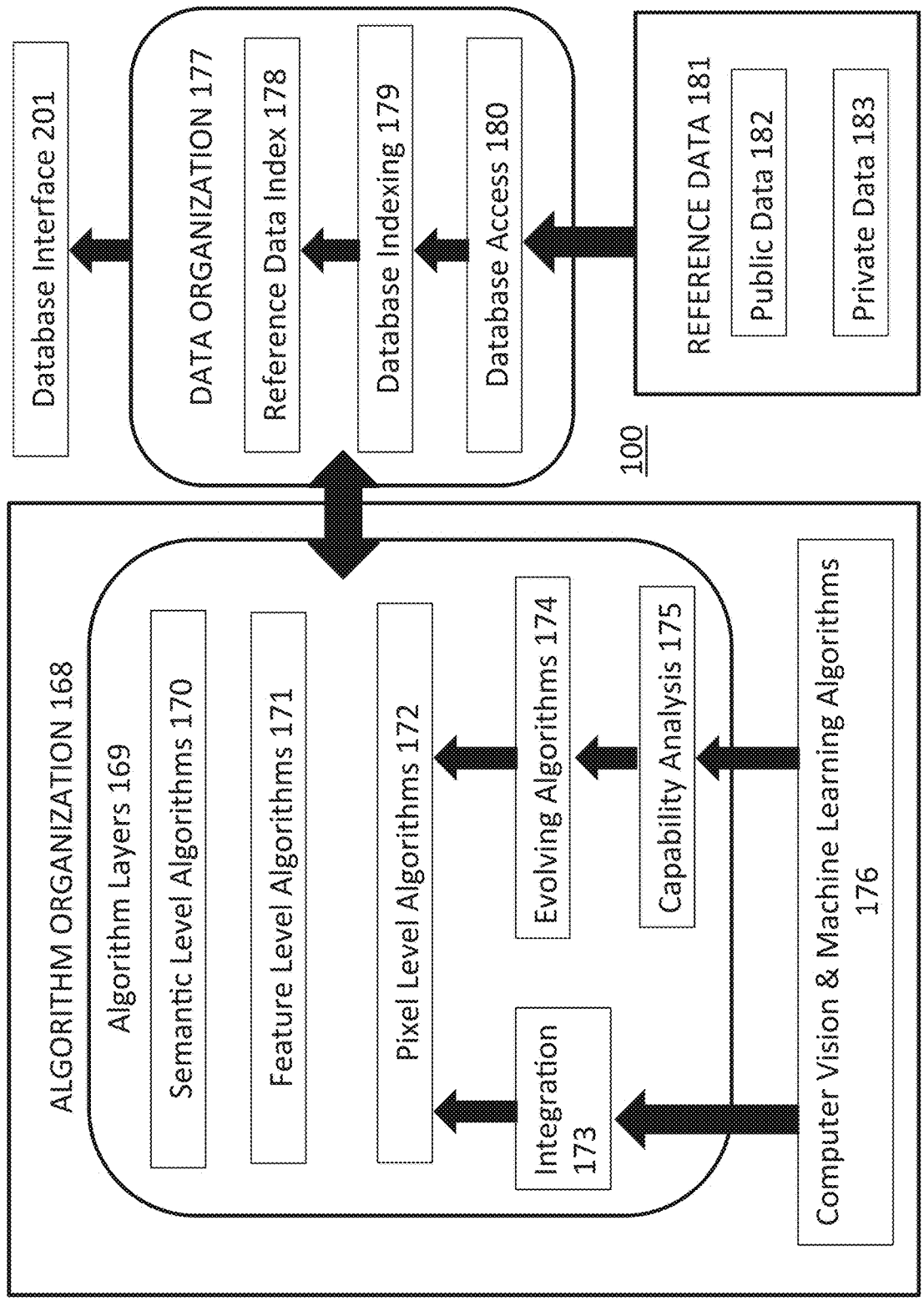
FIG. 15 is a schematic diagram of the system for analyzing items including processing and machine learning framework.

FIG. 15 illustrates the framework of the computer vision and machine learning algorithm layers 169 which organizes algorithms 153 into a pixel-level algorithms 172, feature-level algorithms 171, and semantic-level algorithms 170, where feature-level algorithms 171 are implemented at a higher level of abstraction than pixel-level algorithms 172 and semantic-level algorithms 170 are implemented at a higher level of abstraction than feature-level algorithms 171 and pixel-level algorithms 172. For example, the illustrative pixel-level vision algorithms 172 may produce enhanced versions of input images and may extract camera characteristics; whereas feature-level algorithms 171 may process images to combine feature aggregates and geometry for recognition; and semantic-level algorithms 170 can ingest feature and pixel data to produce decisions, labels or tags, and semantic output.

Integration process 173 integrates algorithms 176 into the layered architecture 169. Capability analysis subsystem 175 evaluates the functional capabilities of computer vision and machine learning algorithms 176 or new versions of computer vision and machine learning algorithms 176 and evolving algorithms function 174 maps the new or new versions of computer vision and machine learning algorithms 176 to an appropriate level algorithms including semantic-level algorithms 170, feature-level algorithms 171 and pixel-level algorithms 172 in algorithm layers 169.

During capability analysis module 175 uses the actual content, such as an image, to predict uncertainty relating to the algorithm's performance of the task of machine learning 145 using coarse feature computations. System for analyzing items 100 can rapidly assess the space of possible solutions, a set of candidate algorithms 154 and assess the final results of executing algorithm 157 selected based on the algorithm type selected from semantic-level algorithms 170, feature-level algorithms 171 and pixel-level algorithms 172 on the content such as the image to perform the task of machine learning 145 using parameters 152. In this way, system for analyzing items 100 enable multiple-level data-driven performance characterization of algorithms for a specific task of machine learning 145. As a result, system for analyzing items 100 can obtain both coarse and fine performance measures to dynamically optimize their processing pipelines by evaluating multiple algorithms such as a set of candidate algorithms.

As an example, for a given "vegetable matching" algorithm, the capability analysis module 175 provides the ranges of achievable location uncertainty with respect to parameters computed from images in the existing datasets. The projected measures are pre-computed for the respective algorithms as part of training and testing stages of the algorithms. For a task of machine learning 145 involving an identity query 141, given images of vegetables, without performing detailed matching, the capability analysis subsystem informs system for analyzing items 100 as to whether the achievable identity certainty is for example 80% or 8%. Capability analysis module 175 produces estimates using other properties of user input 137, such as a query image, such as words that appear on an item label, and also coarse level properties of features related to the task of machine learning 145 such as color or lighting. For example, if an item being queried 137 is in a well-lit area, then it has a much higher chance of being identified by multiple algorithms. Capability analysis module 175 mimics human-like abilities by training system for analyzing items 100 to make high-level estimates based on features of the image.

An embodiment of the capability analysis module 175 can be implemented in multiple stages, including (i) an offline technique for learning the mapping between the image properties and the estimates obtained by running the respective algorithms on labeled examples, and (ii) an incremental technique that can refine its mapping by adding a new image, its properties, and its results. Capability analysis module 175 can dynamically update its predictions by incorporating the results for images previously analyzed by system for analyzing items 100. Given the learned mapping, the capability analysis module 175 computes the global and application-specific features of a test image and applies the mapping to generate estimates of the expected accuracy and confidence.

The estimates produced by capability analysis module 175 are computed from the complete configuration of matching features and determined by combining their confidences and accuracies into summary estimates the capability analysis module 175 analyzes the results of candidate algorithms 153 to estimate a confidence and accuracy for the whole task of machine learning 145. This analysis is different for each task of machine learning 145. For example, when a semantic fingerprint is used to answer an identification task 141 (e.g., query) with respect to an image, the capability analysis module 175 combines the confidences and accuracies associated with each semantic feature detected in the image, such as words on the label of the item or words on the price tags on the shelf, and forms a confidence and accuracy for the whole image. When a word detection algorithm is used, for example, to answer an identity query, capability analysis module 175 reports the expected recall, precision, and confidence of the selected algorithm for the database used.

Reference data 181 can include a wide variety of different content, including the user content, which may be stored in databases, files, and other electronic data stores (which may be referred to herein simply as "data" or "databases" for ease of discussion). Reference data 181 can include private or protected data 183 and public or unprotected data 182.

Referring now to database interface 201 and the data organization subsystem 177, database interface 201 exposes information regarding the content databases of reference data 181 that are available, what type of data each of the databases includes (e.g., area, sensors, biometric data) and the functional characteristics of each of the databases. Some other examples of reference data 181 include: (1) LIDAR (light detection and ranging data), aerial and ground level imagery (with and without any associated metadata); (2) polygonal and point cloud models of objects; (3) biometric and object databases; and (4), botanical, geological, nutritional, and commercial databases. In general, reference data 181 is stored in any suitable computer readable media, such as a data storage device.

Data organization subsystem 177 is embodied as an extensible framework (e.g., middleware) for indexing algorithms to comprehensively and efficiently handle the diversity of databases and data stores of reference data 181 that can be applicable to different applications 130. To do this, data organization subsystem 177 creates reference data 181 by, for example, ingesting data from a large variety of databases and data stores (e.g., Internet sources such as YOUTUBE, FLICKR, FACEBOOK, etc.), where the "ingesting" may be performed by the computing system as an automated (e.g., background) process or by interfacing with an end user, for example. Data organization subsystem 177 automatically indexes data in database indexing module 179 and provides database access interfaces 180 for the applications. For example, database indexing module 179 of data organization subsystem 177 can create reference data index 178 to index a collection of invariant two-dimensional and three-dimensional features as having been demonstrated for accuracy and efficiency. Database access module 180 can specify and verify appropriate permissions and access levels for the applications to access reference data 181, e.g., private data 183 and public data 182. Reference data index 178 automatically indexes visual data and metadata from structured, semi-structured and unstructured data stores. In this way, data organization subsystem 177 can expose a large number of heterogeneous databases and data stores for use by system for analyzing items 100.

Some embodiments of database interface 201 provide multiple types of abstracted APIs that allow unified access to different categories of indexed data, such as: (i) imagery data (e.g., Electro-Optic (EO). Multi-/Hyper-spectral Imagery (MSI/HSI), etc.), (ii) three-dimensional data (e.g., Light Detection and Ranging (LIDAR), Digital Elevation Maps (DEM)), (iii) attributes (e.g., price, location, ingredients, materials), and (iv) features (e.g., Histogram of Oriented Gradients (HoG), spin-image), (iv) object, location, action, event and other such database entity, for instance, locations from a geo-organized imagery database, or actions from an ingested and indexed action database from imagery. For each specific database reference data library 181, database interface 201 exposes certain database information or data, e.g., as a summary table that contains among other fields: data type, or the number of elements in the database. Some embodiments of database interface 201 include an interface to an index of high-dimensional visual and metadata features that enable rapid, typically logarithmic/sublinear, access to the categories of data types described above.

In addition to high-level information or data about the indexed data, the database APIs allow system for analyzing items 100 to poll reference data sources 181 to retrieve stored data according to one or more criteria, such as: (i) spatial or volumetric (e.g., return all the images of ABC Brand Cheese Crackers within a region of interest); (ii) attribute-based (e.g., return all the brands of eggs that came from a local farm); (iii) feature similarity (e.g., return all the baby blankets being similar to input 160); (iv) temporal access. More complex queries can be formed by creating combinations of the different query types.

In some implementations, the APIs for image data use templated image classes to handle different pixel data types (e.g., color, gray scale, etc.). For three-dimensional (3D) data, abstracted 3D point interfaces from open-source libraries can be used. For accessing derived attributes and features, interface 201 may be based on a templated class that comprises several fields, such as: feature identifier, 2D feature location, 3D feature location, origin identifier, descriptor vector or a combination of one or more of these fields. More complex feature types can be constructed using, e.g., inheritance and polymorphism mechanisms to allow APIs to remain fixed.

FIG. 16 illustrates how a vision and learning algorithm services platform 194 is embodied in system 184. The illustrative platform 194 exposes the features and capabilities of a wide variety of computer vision, machine learning, and big data processing algorithms 197 for use by many different types of computer applications 191 at different levels of sophistication, depending on the needs of the particular application 191, user, or the particular application 191 and the user simultaneously. Embodiments of the platform 194 can intelligently provide the needed vision and learning algorithm services to, for example, back-end, middleware, and customer-oriented computer applications.

As used herein, "user-oriented application" may refer to, among other things, any of these types of computer applications, whether back-end, middleware, or customer-oriented computer applications, that has a need for computer vision, machine learning, big data processing, or similar tasks, but whose main focus or objective may be something other than performing computer vision, machine learning, or big data processing tasks. Such applications may include, for example, product recommendations, data-driven image and video content recommenders (e.g., for focused advertising), text recognition applications (e.g., for reading text in images and videos), and others. As used here, "application" or "computer application" may refer to, among other things, any type of computer program or group of computer programs, whether implemented in software, hardware, or a combination thereof, and includes self-contained, vertical, and shrink-wrapped software applications, distributed and cloud-based applications, and others. Portions of a computer application or application may be embodied as firmware, as one or more components of an operating system, a runtime library, an application programming interface (API), as a self-contained software application, or as a component of another software application, for example.

In operation, computer application 191 interfaces with a person, such as an end user or application developer. From time to time, computer application 191 receives or accesses user content 185, which is stored electronically (e.g., as digital files stored in a memory or a data storage device). User content 185 may include, for example, structured (e.g., meta tags) or unstructured (e.g., natural language) text 186, audio 188 (e.g., sounds and spoken dialog), video 187, images 189 (e.g., a single image or a group or sequence of images), bar codes 190, images of text 202 (i.e. letters, numbers, symbols, words) for optical character recognition or a combination of one or more of text 186, audio 188, video 187, images 189, bar codes 190, or images of text 202. Computer application 191 may determine, e.g., by executing computer logic to identify the user content 185 or a characteristic thereof that a computer vision or learning task needs to be performed. If computer application 191 determines that a computer vision or learning task is to be performed, the computer application 191 formulates and submits the vision or learning task 192 to platform 194. As used herein, a "task" may refer to, among other things, an activity, such as a vision or learning operation, to be performed by the computing system 184 on specified content 185. As such, a task can have parameters 199 that relate to, among other things, the specific content 185 to be processed by the computing system 184 in performing the task 192. In some embodiments, task 192 involves executing one or more vision or learning algorithms on the user content 185 and returning a result of the algorithm execution to the requesting application 191. Alternatively, or in addition, task 192 may include a request to select an appropriate algorithm for use in processing particular content 185, and a request to determine an appropriate set of parameters to use with a particular algorithm in processing certain content 185.

Based on the task 192 and zero or more parameters 199 relating to the task 192 (which may be supplied to platform 194 by the application 191 as part of task 192 or separately from the task 192), platform 194 selects one or more of the vision and learning algorithms 197 to perform the task 192. Platform 194 may access reference data 198 in order to inform its algorithm selection process, to perform the requested task 192, or to both access reference data 198 in order to inform its algorithm selection process and to perform the requested task 192. For instance, the platform 194 may utilize reference data 198 to characterize and predict the capabilities of one or more of algorithms 197 in relation to particular task 192. The platform 194 executes or initiates the execution of the selected algorithm(s) 197 to perform the task 192 with the requisite algorithm parameters 195, receives algorithm results 196 (e.g., the output of the execution of the selected algorithm 197), and exposes platform output 193 (e.g., the algorithm results 196 or an "application friendly" version of the algorithm results 196) for use by the computer application 191.

In turn, application 191 may process the platform output 193 according to the needs of the application 191 and, as a result, present application output 200. For example, if the task 192 requested by the application 191 is "recognize all of the items in all of these images," the platform 194 may select an algorithm 197 based on parameters 199, where the parameters 199 may include the number of images 189 to which task 192 relates, the quality or content of the images 189, or the combined quality and content of the images 189, the processing power of the available computing resources (e.g., mobile device or server), the task type (e.g. object, scene, or activity recognition) or a combination of the available computing resources and the task type. The selected algorithm 197 performs the task 192 by, for instance, algorithmically extracting useful information or data from the images 189 and comparing the useful information or data for each of the images 189 to a portion of the reference data 198. Platform 194 may supply the matching images or information or data relating to the matching images (such as the name of each item recognized in each of the images 189, or a computer storage location at which the matching images can be accessed) to the application 191 as platform output 193. Application 191 may formulate the platform output 193 for presentation to an end user of application 191. For instance, the application 191 may place the recognized items' names on or adjacent to each image 189 and display image 189 and recognized name on a display device of computing system 184 or the application 191 may invoke a text-to-speech processor to output the recognized items' names as machine-generated speech audio. Alternatively, and in addition, application 191 may use the name information or data for a subsequent task, such as to rate the item or to query other information or data relating to the item. The manner in which application 191 ultimately utilizes the platform output 193 can vary depending on the requirements or design of the particular application 191.

Embodiments of platform 194 ensure that the requested task 192 is completed within the requisite accuracy, quality, efficiency, and other parameters that may be specified by application 191 as part of the task 192 and other parameters 199. Any application 191 that has a need for vision or learning algorithm services can benefit from the use of platform 194. In some implementations, revenue may be generated in response to the use of platform 194 and underlying algorithms 197 by various applications 191. For example, medical research organizations may want to use these vision and learning algorithms 197 for patient behavior studies, and the selection of an algorithm may trigger a revenue event.

Other examples include but are not limited to collecting and analyzing data concerning purchases and consumption of s between a specific person and a reference population and collecting and analyzing item data and user data for private and public entities such as retailers, manufacturers, government agencies, medical facilities, etc. for large-scale data analysis (e.g. collecting, storing and analyzing user data and item data such as consumer demographics, purchases, medical history, health status, biomedical information or data, prices, location, inventory, availability, product reviews, recipes, etc. in order for retailers and manufacturers to hone their business and marketing strategies and locate products, track inventory, analyze customer traffic, gauge customer interest, and the like).

Another example in which application 191 utilizes platform output 193 within system for analyzing items 100 is collecting data such as quantities of items and the location of items for private and public organizations, as well as government entities when items are recalled to signal users, retailers and manufacturers to the recalled items by location. When system for analyzing items 100 recognizes an item that has been recalled by a user's computing device, the location of that user and item is reported back to the system, allowing manufacturers and retailers to quickly pinpoint the locations of recalled items that are still on store shelves, so they can quickly remove the recalled items to protect consumers' safety.

Another example in which application 191 utilizes the platform output 193 within system for analyzing items 100 includes collecting and analyzing data for retailers and manufacturers about the frequency of their products being considered by customers and, in turn, the frequency that those products are purchased by customers or are passed over by customers in order to know customers' ultimate product choice was. Retailers and manufacturers can use this data for example, to figure out if they need to encourage customers to increase their purchase frequency of a product or if the marketing strategy should focus more on increasing the number of households that purchase the product.

Another example in which application 191 utilizes platform output 193 within system for analyzing items 100 includes collecting data about purchases of items and consumption of items so that in the event of an outbreak, such as an *e-coli* outbreak, the source of the outbreak, such as a certain farm, can be tracked down quickly and at-risk items can be removed for public safety.

Another important example in which application 191 utilizes platform output 193 within system for analyzing items 100 includes collecting, storing, analyzing, and displaying information or data about items to assist public and private entities including, but not limited to, retailers, manufacturers, eating establishments and government entities to help them comply with and enforce federal, state, and local regulations. For example, system for analyzing items 100 may be used by the United States Federal Drug Administration (FDA) to enforce the Nutrition Labeling of Standard Menu Items in Restaurants and Similar Retail Food Establishments regulation. In another example, system for analyzing items 100 may assist the United States Department of Agriculture (USDA) identify which items meet the USDA's standards for classifications that include, but are not limited to, "Certified Organic," "Non-GMO," "Certified Vegan," "Fair Trade," "Kosher," etc.

General Considerations

In the foregoing description, numerous specific details, examples, and scenarios are set forth in order to provide a more thorough understanding of the present disclosure. It will be appreciated, however, that embodiments of the disclosure may be practiced without such specific details. Further, such examples and scenarios are provided for illustration, and are not intended to limit the disclosure in any way. Those of ordinary skill in the art, with the included descriptions, should be able to implement appropriate functionality without undue experimentation.

References in the specification to "an embodiment," etc., indicate that the embodiment described may include a particular feature, structure, or characteristic, but every embodiment may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to affect such feature, structure, or characteristic in connection with other embodiments whether or not explicitly indicated.

Embodiments in accordance with the disclosure may be implemented in hardware, firmware, software, or any combination thereof. Embodiments may also be implemented as instructions stored using one or more machine-readable media, which may be read and executed by one or more processors. A machine-readable medium or device may include any mechanism for storing or transmitting information or data in a form readable by a machine (e.g., a computing device or a "virtual machine" running on one or more computing devices). For example, a machine-readable medium may include any suitable form of volatile or non-volatile memory.

Modules, data structures, blocks, and the like are referred to as such for ease of discussion, and are not intended to imply that any specific implementation details are required. For example, any of the described modules and data structures may be combined or divided into sub-modules, sub-processes or other units of computer code or data as may be required by a particular design or implementation. In the drawings, specific arrangements or orderings of schematic elements may be shown for ease of description. However, the specific ordering or arrangement of such elements is not meant to imply that a particular order or sequence of processing, or separation of processes, is required in all embodiments. In general, schematic elements used to represent instruction blocks or modules may be implemented using any suitable form of machine-readable instruction, and each such instruction may be implemented using any suitable programming language, library, application-programming interface (API), and other software development tools or frameworks. Similarly, schematic elements used to represent data or information or data may be implemented using any suitable electronic arrangement or data structure. Further, some connections, relationships or associations between elements may be simplified or not shown in the drawings so as not to obscure the disclosure. This disclosure is to be considered as exemplary and not restrictive in character, and all changes and modifications that come within the spirit of the disclosure are desired to be protected.

What is claimed is:

1. A system for analyzing a plurality of items comprising;
  a computing device, the computing device including an image sensor configured to sense an image of each of a plurality of items, the plurality of items including at least one food item and at least one non-food item, the computing device including at least one processor; and
  the computing device including analysis instructions that when executed by the at least one processor in response to a user request cause data analysis of the sensed image of each of the plurality of items through searching and acquiring an item analysis from one or more databases, API's, web services, cloud services, machine learning and algorithms, the data analysis provides data on one or more components of ingredients, health conditions, food type, mineral type, serving size, nutrition facts, nutrition information, total ingredient information, meal planning, exercise planning and caloric expenditure, the data analysis processing the data associated with the identification of the plurality of items with one or more parameters, the parameters being selected from one or more of health conditions, food or mineral type, materials, ingredients, nutrition facts, nutrition information, lifestyle preferences, dietary restrictions, dietary preferences, cultural preferences religious preferences, customizable user preferences, locations of origin, material source, availability, cost, location, inventory status, recall status, color, flavor, size, pattern, ability to be delivered, brand information, discounts, promotions, features, customer reviews, recipes, investigations, lawsuits, serving size, number purchased, frequency of purchase of the plurality of items, frequency of search of the plurality of items, meal type, item category, manufacturing information, comparison tools, and caloric expenditure, the one or more components are used to analyze how the plurality of items affect health, the data analysis determines a rating of the plurality of items based on the analysis of how the plurality of items affect health, and cause display of the sensed image of each of the plurality of items and the rating on a visual display of the computing device, the rating comprising one or more numbers, colors, words, shapes or symbols, the rating being displayed on the visual display as an image superimposed over each of the displayed sensed images of the plurality of items.

2. The system of claim 1 wherein the computing device is selected from a smart phone, tablet, computer, laptop, smart watch, smart glasses, or virtual reality viewing devices.

3. The system of claim 1 wherein the computing device is configured to hover or be near the plurality of items in order for the image sensor to recognize the plurality of items and return the data analysis of each of the plurality of items to the visual display.

4. The system of claim 1 wherein the data analysis further comprises one or more additional ratings, the one or more additional ratings comprising one or more numbers, words, shapes or symbols.

5. The system of claim 4 wherein the rating and the additional rating indicates a favorable or unfavorable rating.

6. The system of claim 1 wherein the rating includes one or more colors, the data analysis includes determining a scale of the one or more colors, the scale being displayed on the visual display as a scale that is color-coded or numeric.

7. The system of claim 1 wherein the data analysis includes identification of the sensed images of the plurality of items and data associated with the identification of the plurality of items by one or more of image recognition, optical character recognition, voice recognition, typed query or a bar code scan.

8. The system of claim 1 wherein the data analysis further determines an audible rating, the audible rating being delivered as an audible communication on an audible communication device, the audible communication comprises one or more of sound effects, songs, spoken words and spoken sentences.

9. The system of claim 1 wherein having the item or an image of the plurality of items within the field of view of the sensor activates the data analysis.

10. The system of claim 1 wherein the sensed image of the plurality of items is captured by taking a photo of a plurality of items with the computing device and the captured photo is input to the data analysis.

11. The system of claim 1 wherein the image of the plurality of items is an image, picture, video or visual display on a television, computer monitor, computing device or virtual reality device.

12. The system of claim 1 wherein the data analysis includes an add item feature to add the item analysis to a log.

13. The system of claim 1 wherein the data analysis provides data on the one or more components further comprising, item category, materials, material sources, medical studies, recipes, lifestyle preferences, cultural preferences, religious preferences, user preferences, other users' preferences, cooking instructions, cooking advice, shopping lists, customer reviews, investigations, lawsuits, location of the plurality of items, cost, availability, location of origin, number purchased, manufacturing information, comparison tools, frequency of search for the plurality of items, frequency of purchase of the plurality of plurality of items, price per unit, inventory status, ability to be delivered, brand information, discounts, promotions, and recall status.

14. The system of claim 1 wherein the data analysis creates, displays or allows submission of reviews of an item, a list of ingredients or components of an item and the list of ingredients or components is selected to provide data on the ingredient or the component, the data being information about one or more of medical studies, health conditions, recipes, lifestyle preferences, cultural preferences, religious preferences, user preferences, other users' preferences, cooking instructions, cooking advice, shopping lists, customer reviews, investigations, lawsuits, location of the plurality of items, cost, availability, serving size, nutrition information, total ingredient information, location of origin, number purchased, manufacturing information, comparison tools, frequency of search for the plurality of items, frequency of purchase, meal planning, exercise planning, caloric expenditure, price per unit, food or mineral type, category, materials, material sources, brand information, and recall status.

15. The system of claim 1 wherein the data analysis displays a feature, an increase execution tool is used to increase the feature and a decrease execution tool is used to decrease the feature.

16. The system of claim 1 further comprising an audio sensor for submitting audio data on the plurality of items, the analysis instructions that when executed by the at least one processor in response to a user request cause data analysis of the audio data of each of the plurality of items through searching and acquiring an item analysis from one or more databases, API's, web services, cloud services, machine learning and algorithms and cause display of the data analysis on the visual display of the computing device and the audible communication on the audible communication device or cause display of the data analysis through the combination of the visual display of the computing device and the audible communication on the audible communication device.

17. The system of claim 1 wherein the computing device comprises a keyboard for submitting typed data on the plurality of items, the analysis instructions that when executed by the at least one processor in response to a user request cause data analysis of the typed data of each of the plurality items through searching and acquiring an item analysis from one or more databases, API's, web services, cloud services, machine learning and algorithms and cause display of the data analysis on the visual display of the computing device.

18. The system of claim 1 further comprising display of the data analysis using a tactile function of the computing device, the tactile function being a series of vibrations.

19. The system of claim 1 wherein one or more features of the data analysis are logged.

20. The system of claim 1 wherein the plurality of items are information to assist the public and provide entities the data analysis comprised of collecting, storing and analyzing the information.

21. The system of claim 1 wherein the data analysis can be shared between a plurality of users of the system.

22. The system of claim 1 wherein one or more features of the data analysis are used for purchasing items, purchasing alternative items, and keeping track of purchases and spending.

23. The system of claim 1 wherein one or more features of the data analysis are used in applications for governmental, marketing, retail or manufacturing.

24. The system of claim 1 wherein one or more features of the data analysis are used to identify which governmental certifications and organizational certifications the plurality of items are eligible for or qualify under.

25. A system for analyzing one or more items comprising; a computer device, the computing device including an image sensor configured to sense an image of each of the one or more items, the computing device Including at least one processor; and the computing device including analysis instructions that when executed by the at least one processor in response to a user request cause data analysis of the sensed image of each of the one or more items through searching and acquiring an item analysis from one or more databases, API's, web services, cloud services, machine learning and algorithms, the data analysis provides data on one or more components of ingredients, health conditions, food type, mineral type, serving size, nutrition facts, nutrition information, total ingredient information, meal planning, exercise planning and caloric expenditure, the one or more components are used to analyze how the one or more items affect health, the data analysis determines a rating of the one or more items based on the analysis of how the one or more items affect health, and cause display of the sensed image of each of the one or more items and the rating on a visual display of the computing device, the rating comprising one or more number, colors, words, shapes or symbols, the rating being displayed on the visual display as an image superimposed over each of the displayed sensed images of the one or more items wherein the data analysis includes an alternative item feature to access an item analysis of one or more alternative items.

26. The system of claim 25 wherein the computing device is selected from a smart phone, tablet, computer, laptop, smart watch, smart glasses, or virtual reality viewing devices.

27. The system of claim 25 wherein the computing device is configured to hover or be near the one or more items in order for the image sensor to recognize the one or more items and return the data analysis of each of the one or more items to the visual display.

28. The system of claim 25 wherein the data analysis further comprises one or more additional ratings, the one or more additional ratings comprising one or more numbers, words, shapes or symbols.

29. The system of claim 28 wherein the rating and the additional rating indicates a favorable or unfavorable rating.

30. The system of claim 25 wherein the rating includes one or more colors, the data analysis includes determining a scale of the one or more colors, the scale being displayed on the visual display as a scale that is color-coded or numeric.

31. The system of claim 25 wherein the data analysis includes identification of the sensed images of the one or more items and data associated with the identification of the one or more items by one or more of image recognition, optical character recognition, voice recognition, typed query or a bar code scan.

32. The system of claim 25 wherein the data analysis further determines an audible rating, the audible rating being delivered as an audible communication on an audible communication device, the audible communication comprises one or more of sound effects, songs, spoken words and spoken sentences.

33. The system of claim 25 wherein having the item or an image of the one or more items within the field of view of the sensor activates the data analysis.

34. The system of claim 25 wherein the sensed image of the one or more items is captured by taking a photo of the one or more items with the computing device and the captured photo is input to the data analysis.

35. The system of claim 25 wherein the image of the one or more items is an image, picture, video or visual display on a television, computer monitor, computing device or virtual reality device.

36. The system of claim 25 wherein the data analysis includes an add item feature to add the item analysis to a log.

37. The system of claim 25 wherein the data analysis provides data on the one or more components further comprising, item category, materials, material sources, medical studies, recipes, lifestyle preferences, cultural preferences, religious preferences, user preferences, other users' preferences, cooking instructions, cooking advice, shopping lists, customer reviews, investigations, lawsuits, location of the one or more items, cost, availability, location of origin, number purchased, manufacturing information, comparison tools, frequency of search for the one or more items, frequency of purchase of the one or more items, price per unit, inventory status, ability to be delivered, brand information, discounts, promotions, and recall status.

38. The system of claim 25 wherein the data analysis creates, displays or allows submission of reviews of an item, a list of ingredients or components of an item and the list of ingredients or components is selected to provide data on the ingredient or the component, the data being information about one or more of medical studies, health conditions, recipes, lifestyle preferences, cultural preferences, religious preferences, user preferences, other users' preferences, cooking instructions, cooking advice, shopping lists, customer reviews, investigations, lawsuits, location of the one or more items, cost, availability, serving size, nutrition information, total ingredient information, location of origin, number purchased, manufacturing information, comparison tools, frequency of search for the one or more items, frequency of purchase, meal planning, exercise planning, caloric expenditure, price per unit, food or mineral type, category, materials, material sources, brand information, and recall status.

39. The system of claim 25 further comprising an audio sensor for submitting audio data on the one or more items, the analysis instructions that when executed by the at least one processor in response to a user request cause data analysis of the audio data of each of the one or more items through searching and acquiring an item analysis from one or more databases, API's, web services, cloud services, machine learning and algorithms and cause display of the data analysis on the visual display of the computing device and the audible communication on the audible communication device or cause display of the data analysis through the combination of the visual display of the computing device and the audible communication on the audible communication device.

40. The system of claim 25 wherein the computing device comprises a keyboard for submitting typed data on the one or more items, the analysis instructions that when executed by the at least one processor in response to a user request cause data analysis of the typed data of each of the one or more items through searching and acquiring an item analysis from one or more databases, API's, web services, cloud services, machine learning and algorithms and cause display of the data analysis on the visual display of the computing device.

41. The system of claim 25 further comprising display of the data analysis using a tactile function of the computing device, the tactile function being a series of vibrations.

42. The system of claim 25 wherein one or more features of the data analysis are logged.

43. The system of claim 25 wherein the one or more items are information to assist the public and provide entities the data analysis comprised of collecting, storing and analyzing the information.

44. The system of claim 25 wherein the data analysis can be shared between a plurality of users of the system.

45. The system of claim 25 wherein one or more features of the data analysis are used for purchasing items, purchasing alternative items, and keeping track of purchases and spending.

46. The system of claim 25 wherein one or more features of the data analysis are used in applications for governmental, marketing, retail or manufacturing.

47. The system of claim 25 wherein one or more features of the data analysis are used to identify which governmental certifications and organizational certifications the one or more items are eligible for or qualify under.

48. A system for analyzing one or more items comprising; a computing device, the computing device including an image sensor configured to sense an image of each of the one or more items, the computing device including at least one processor, and the computing device including analysis request cause data analysis of the sensed image of each of the one or more items through searching and acquiring an item analysis from one or more databases, API's, web services, cloud services, machine learning and algorithms, the data analysis provides data on one or more components of ingredients, health conditions, food type, mineral type, serving size, nutrition facts, nutrition information, total ingredient information, meal planning, exercise planning and caloric expenditure, the one or more components are used to analyze how the one or more items affect health, the data analysis determines a rating of the one or more items based on the analysis of how the one or more items affect health, and cause display of the sensed image of each of the one or more items and the rating on a visual display of the computing device, the rating comprising one or more numbers, colors, words, shapes or symbols, the rating being displayed on the visual display as an image superimposed over each of the displayed sensed images of the one or more items wherein the computing device comprises a bar code scanner for submitting a bar code on the one or more items, the analysis instructions that when executed by the at least one processor in response to a user request cause data analysis of the bar code of each of the one or more items through searching and acquiring an item analysis from one or more databases, API's, web services, cloud services, machine learning and algorithms and cause display of the data analysis on the visual display of the computing device.

49. The system of claim 48 wherein the data analysis displays a feature, an increase execution tool is used to increase the feature and a decrease execution tool is used to decrease the feature.

50. The system of claim 48 wherein the computing device is selected from a smart phone, tablet, computer, laptop, smart watch, smart glasses, or virtual reality viewing devices.

51. The system of claim 48 wherein the computing device is configured to hover or be near the one or more items in order for the image sensor to recognize the one or more items and return the data analysis of each of the one or more items to the visual display.

52. The system of claim 48 wherein the data analysis further comprises one or more additional ratings, the one or more additional ratings comprising one or more numbers, words, shapes or symbols.

53. The system of claim 52 wherein the rating and the additional rating indicates a favorable or unfavorable rating.

54. The system of claim 48 wherein the rating includes one or more colors, the data analysis includes determining a scale of the one or more colors, the scale being displayed on the visual display as a scale that is color-coded or numeric.

55. The system of claim 48 wherein the data analysis further determines an audible rating, the audible rating being delivered as an audible communication on an audible communication device, the audible communication comprises one or more of sound effects, songs, spoken words and spoken sentences.

56. The system of claim 48 wherein the data analysis includes an add item feature to add the item analysis to a log.

57. The system of claim 48 wherein the data analysis provides data on the one or more components further comprising, item category, materials, material sources, medical studies, recipes, lifestyle preferences, cultural preferences, religious preferences, user preferences, other users' preferences, cooking instructions, cooking advice, shopping lists, customer reviews, investigations, lawsuits, location of the one or more items, cost, availability, location of origin, number purchased, manufacturing information, comparison tools, frequency of search for the one or more items, frequency of purchase of the one or more items, price per unit, inventory status, ability to be delivered, brand information, discounts, promotions, and recall status.

58. The system of claim 48 wherein the data analysis creates, displays or allows submission of reviews of an item, a list of ingredients or components of an item and the list of ingredients or components is selected to provide data on the ingredient or the component, the data being information about one or more of medical studies, health conditions, recipes, lifestyle preferences, cultural preferences, religious preferences, user preferences, other users' preferences, cooking instructions, cooking advice, shopping lists, customer reviews, investigations, lawsuits, location of the one or more items, cost, availability, serving size, nutrition information, total ingredient information, location of origin, number purchased, manufacturing information, comparison tools, frequency of search for the one or more items, frequency of purchase, meal planning, exercise planning, caloric expenditure, price per unit, food or mineral type, category, materials, material sources, brand information, and recall status.

59. The system of claim 48 wherein the data analysis displays a feature, an increase execution tool is used to increase the feature and a decrease execution tool is used to decrease the feature.

60. The system of claim 48 further comprising an audio sensor for submitting audio data on the one or more items, the analysis instructions that when executed by the at least one processor in response to a user request cause data analysis of the audio data of each of the one or more items through searching and acquiring an item analysis from one or more databases, API's, web services, cloud services, machine learning and algorithms and cause display of the data analysis on the visual display of the computing device and the audible communication on the audible communication device or cause display of the data analysis through the combination of the visual display of the computing device and the audible communication on the audible communication device.

61. The system of claim 48 further comprising display of the data analysis using a tactile function of the computing device, the tactile function being a series of vibrations.

62. The system of claim 48 wherein one or more features of the data analysis are logged.

63. The system of claim 48 wherein the one or more items are information to assist the public and provide entities the data analysis comprised of collecting, storing and analyzing the information.

64. The system of claim 48 wherein the data analysis can be shared between a plurality of users of the system.

65. The system of claim 48 wherein one or more features of the data analysis are used for purchasing items, purchasing alternative items, and keeping track of purchases and spending.

66. The system of claim 48 wherein one or more features of the data analysis are used in applications for governmental, marketing, retail or manufacturing.

67. The system of claim 48 wherein one or more features of the data analysis are used to identify which governmental certifications and organizational certifications the one or more items are eligible for or qualify under.

* * * * *